US006518476B1

(12) United States Patent
Culp et al.

(10) Patent No.: US 6,518,476 B1
(45) Date of Patent: Feb. 11, 2003

(54) METHODS FOR MANUFACTURING OLEFINS FROM LOWER ALKANS BY OXIDATIVE DEHYDROGENATION

(75) Inventors: Gary Lynn Culp, Kenna, WV (US); Vincent Joseph Stricker, Charleston, WV (US); James Russell Nelson, Charleston, WV (US); Madan Mohan Bhasin, Charleston, WV (US); Kenneth Andrew Nielsen, Charleston, WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 136 days.

(21) Appl. No.: 09/664,530

(22) Filed: Sep. 18, 2000

(51) Int. Cl.[7] ............................ C07C 5/327; C07C 5/333
(52) U.S. Cl. ........................ 585/655; 585/658; 585/661; 585/662; 585/663; 585/943
(58) Field of Search ................................. 585/655, 658, 585/661, 662, 663, 943

(56) References Cited

U.S. PATENT DOCUMENTS

| | | | |
|---|---|---|---|
| 3,456,032 A | 7/1969 | Kniel | 585/650 |
| 4,174,353 A | 11/1979 | Marcinkowsky et al. | 585/835 |
| 4,547,607 A | 10/1985 | Jones et al. | 585/500 |
| 4,554,395 A | 11/1985 | Jones et al. | 585/500 |
| 4,695,668 A | 9/1987 | Velenyi | 585/500 |
| 4,754,093 A | 6/1988 | Jezl et al. | 585/500 |
| 4,808,563 A | 2/1989 | Velenyi | 502/241 |
| 5,025,108 A | 6/1991 | Cameron et al. | 585/500 |
| 5,066,629 A | 11/1991 | Lukey et al. | 502/84 |
| 5,068,486 A | 11/1991 | Han et al. | 585/500 |
| 5,118,898 A | 6/1992 | Tyler et al. | 585/500 |
| 5,254,781 A | 10/1993 | Calamur et al. | 585/500 |
| 5,336,825 A | 8/1994 | Choudhary et al. | 585/500 |
| 5,736,107 A | 4/1998 | Inomata et al. | 422/144 |
| 5,859,304 A | 1/1999 | Barchas et al. | 585/809 |

OTHER PUBLICATIONS

Walsh, D.E., et al., "Direct Oxidative Methane Conversion at Elevated Pressure and Moderate Temperatures", *Ind. Eng. Chem. Res. 1992, 31, 1259–1262.*
Walsh, D.E., "Pressure, Temperature, and Product Yield Relationships in Direct Oxidative Methane Conversion at Elevated Pressures and Moderate Temperatures", *Ind. Eng. Chem. Res. 1992, 31, 2422–2425.*
Ekstrom, A., et al., "Effect of Pressure on the Oxidative Coupling Reaction of Methane", *Applied Catalysis, 62 (1990) 253–269.*
Liu, Y. et al., "Direct Epoxidation on Ethylene in a Dilute Reaction Stream in Oxidative Coupling of Methane", *Applied Catalysis A: General 121 (1995) 57–68.*
Cordi, E.M., et al., "Steady–State Production of Olefins in High Yields During the Oxidative Coupling of Methane: Utilization of a Membrane Contactor", *Applied Catalysis A: General 155 (1997) L1–L7.*

(List continued on next page.)

Primary Examiner—Thuan D. Dang

(57) ABSTRACT

The present invention provides methods for manufacturing olefins such as ethylene and propylene from lower alkanes, that is, methane, ethane and/or propane, by oxidative dehydrogenation at elevated pressure. The olefins are selectively recovered from unconverted lower alkane feed and reaction byproducts by using a complexation separation, such as an absorption separation that uses aqueous silver nitrate as the complexation agent. Catalysts are used that give high selectivity for oxidative dehydrogenation of lower alkanes to olefins at elevated pressure, such as a nonstoichiometric rare earth oxycarbonate catalyst.

31 Claims, 6 Drawing Sheets

OTHER PUBLICATIONS

Hall, R.B., et al., "Effects of Product Separation on the Kinetics and Selectivity of Oxidative Coupling", *Methane and Alkane Conversion Chemistry, Corporate Research Laboratories, Exxon Research Co. p. 123–130.*

Keller, G.E. et al., "Synthesis of Ethylene via Oxidative Coupling of Methane", *Journal of Catalysis 73, 9–19 (1982).*

Matherne, J.L. et al., "Direct Conversion of Methane to C2's and Liquid Fuels: Process Economics", *Union Carbide Chemicals and Plastics Company, Inc., So. Charleston, WV, 14, pp. 463–482.*

Pinabiau–Carlier, M. et al., "The Effect of Total Pressure on the Oxidative Coupling of Methane Reaction Under Cofeed Conditions", *A. Holmen et al. (Editors), Natural Gas Conversion (1991), pp. 183–190.*

METHODS FOR MANUFACTURING OLEFINS FROM LOWER ALKANS BY OXIDATIVE DEHYDROGENATION

FIELD OF THE INVENTION

This invention relates, in general, to manufacturing olefins from lower alkanes. As used herein, the term "olefins" means ethylene, propylene, butenes, pentenes, hexenes and higher olefins. The term "lower alkanes" means methane, ethane and/or propane. More particularly, the present invention relates to methods for manufacturing olefins such as ethylene and propylene from methane, ethane, and/or propane by oxidative dehydrogenation at elevated pressure, wherein the olefins are recovered from unconverted methane, ethane, and/or propane and reaction byproducts by using a complexation separation. In one embodiment of the invention, recycle of reaction byproducts is reduced or eliminated by adding an effluent containing unconverted methane, ethane, and/or propane and reaction byproducts to a methane gas transport system, such as a natural gas pipeline.

BACKGROUND OF THE INVENTION

Methane is an attractive raw material because it is widely available and inexpensive; however, it is used mainly as a fuel. Natural gas liquids, such as ethane and propane, are the major raw materials for the production of ethylene and propylene, from which many petrochemicals are produced. But the supply of natural gas liquids has not kept pace with increasing demand for olefins, so more costly cracking processes that use naphtha from petroleum are being commercialized. Therefore, the development of economical processes for manufacturing olefins from methane and other lower alkanes is highly desirable.

Methane has low chemical reactivity, so severe conditions are required to convert it to higher hydrocarbons such as olefins. Oxidative dehydrogenation is favored because conversion is not thermodynamically limited and reactions are exothermic. But selectively producing ethylene by partial oxidation, while avoiding over-oxidation to carbon oxides, has been elusive and is difficult to achieve. Therefore, since the first screening of oxidative dehydrogenation coupling catalysts was reported by G. E. Keller and M. M. Bhasin in "Synthesis of Ethylene via Oxidative Coupling of Methane. I. Determination of Active Catalysts", *Journal of Catalysis* 73: 9–19 (1982), great effort has been made to develop selective catalysts and processes for methane coupling.

Catalyst studies have nearly all been at atmospheric pressure, with only a few studies conducted at elevated pressure. This is the case because it has been reported that increasing pressure reduces coupling selectivity, primarily due to increased homogeneous or heterogeneously catalyzed combustion. The oxidative dehydrogenation coupling reaction is highly exothermic, and a high reaction temperature is usually generated within a hot spot after the reactants are heated to the initiation temperature. The temperatures employed generally exceed 650° C. and are typically 800 to 900° C. An important catalyst characteristic is lifetime, especially under such high temperature conditions. Sustained operation at excessively high temperatures usually causes significant to substantial decay in selectivity and may also result in the loss of catalytic and promoter components through slow-to-rapid vaporization.

Process studies have developed cofeed (continuous) processes and sequential (pulsed) processes. The cofeed processes pass methane and oxygen simultaneously over a catalyst in a fixed-bed or fluidized-bed reactor. They typically use low methane conversion for safety and because olefin selectivity decreases as conversion increases. The reactions are operated under oxygen-limited conditions, i.e., very high or total oxygen conversion. The sequential processes alternately contact the catalyst with oxygen (oxidation) and then methane (reduction), either in cyclic pulses or in separate reactors. Because methane does not contact gaseous oxygen in sequential processes, homogeneous oxidation is suppressed, and conversion can be higher.

Sequential catalysts are typically reducible metal oxides that function as oxygen transfer agents. Materials that have been used as sequential catalysts include a wide variety of reducible metal oxides, mixed metal oxides and other reducible compounds of the following metals: Sn, Pb, Bi, Tl, Cd, Mn, Sb, Ge, In, Ru, Pr, Ce, Fe, Re, Tb, Cr, Mo, W, V or mixtures thereof. Promoters include oxides or compounds containing alkali metals, alkaline earth metals, boron, halogens, Cu, Zr, or Rh. Processes which utilize a reducible metal oxide catalyst are disclosed, for example, in the following references: U.S. Pat. No. 4,547,607 discloses methane coupling wherein a portion of the $C_2+$ alkanes recovered are subsequently recycled to the reactor. No examples under pressure are given. U. S. Pat. No. 4,554,395 discloses methane coupling at elevated pressure (100 psig and 700° C.) to promote formation of $C_3+$ hydrocarbons, but does not disclose the effect on $C_2$ hydrocarbons. The higher $C_3+$ selectivity decreases considerably after just a few minutes. U.S. Pat. No. 4,754,093 discloses reacting methane and air, adsorbing higher hydrocarbons on activated carbon at atmospheric pressure, selectively desorbing olefins under vacuum, and recycling higher alkanes with the uncoverted methane.

Many metal oxides, carbonates, and promoted mixtures, often supported on substrates such as alumina, silica, and titania, have been used as cofeed catalysts for oxidative dehydrogenation coupling. These include alkaline earth metal oxides, alkali metal oxides or halides, and oxides of Mn, Co, Ni, Zn, Bi, Pb, Sb, Sn, Tl, In, Cd, Ge, Be, Ca, Sr, Ba, Sc, Y, Zr, La, Nd, Sm, Eu, Gd, Dy, Ho, Er, Tm, Yb, or Lu, either individually or as mixtures thereof. Other metal-containing materials such as various zeolites have also been used. The metal oxides are often promoted with alkali metals and/or alkaline earth metals or their oxides, halides, or carbonates. Basic oxides promoted with alkali metal carbonates are important catalysts, as well as transition metal compounds.

Cofeed catalysts and oxidative dehydrogenation coupling processes utilizing such catalysts are disclosed, for example, in the following references: U.S. Pat. Nos. 4,695,668 and 4,808,563 disclose catalysts containing Mo-W compounds, which gave $C_2$ and oxygenated hydrocarbons, and much CO, at 520 to 800 psig. U.S. Pat. Nos. 5,066,629 and 5,118,898 disclose separating natural gas into methane and higher alkanes, oxidatively coupling the methane, pyrolyzing the higher alkanes by using the heat released, cryogenically separating the combined products, and recycling recovered ethane to the pyrolysis reaction. Integrated processes for converting natural gas into higher hydrocarbons are further disclosed in U.S. Pat. Nos. 5,025,108; 5,254,781; 5,736,107; and 5,336,825. The latter discloses recycling, to the coupling reaction, which is preferably done at 1–2 atmospheres pressure, the methane and $C_2$ hydrocarbons left over from subsequently converting the olefins to liquid hydrocarbons. Note also, J. L. Matherne and G. L. Culp, "Direct Conversion of Methane to $C_2$'s and Liquid Fuels:

Process Economics", pages 463–482, in E. E. Wolf, *Methane Conversion by Oxidative Processes, Fundamental and Engineering Aspects*, Van Nostrand Reinhold (1992).

A number of these prior art references disclose recycling unconverted methane containing byproduct alkanes to the oxidative dehydrogenation coupling reaction. These references suggest that the reaction may be done under elevated pressure, but they do not demonstrate that recycling such a composition is feasible or beneficial when the reaction is done under elevated pressure. Furthermore, the aforementioned processes that demonstrate conducting the oxidative dehydrogenation coupling reaction under elevated pressure do not suggest or demonstrate recycling unconverted methane containing byproduct alkanes to the reaction. The aforementioned processes also disclose cryogenic distillation separation, adsorption/desorption separation using activated carbon or charcoal, and separation by subsequent olefin reaction as methods by which olefins may be separated from unconverted methane and byproduct alkanes, but they do not disclose using complexation separation methods.

Several literature studies have found that operating the oxidative dehydrogenation coupling reaction under elevated pressure reduces $C_2$ selectivity and/or catalyst activity. G. J. Hutchings, et al., "The Role of Gas Phase Reaction in the Selective Oxidation of Methane", *Journal of the Chemical Society, Chemical Communications* 1988: 253, found that $C_2$ selectivity was higher without using a Li/MgO catalyst at 85 psi. A. Ekstrom, et al., "Effect of Pressure on the Oxidative Coupling Reaction of Methane", *Applied Catalysis* 62: 253 (1990), found that increasing pressure to 87 psi depressed $C_2+$ selectivity and catalyst activity for Li/MgO, $Sm_2O_3$, and $SrCO_3/Sm_2O_3$ catalysts, by increasing uncatalyzed combustion. M. Pinabiau-Carlier, et al., "The Effect of Total Pressure on the Oxidative Coupling of Methane Reaction Under Cofeed Conditions", pages 183–190 in A. Holmen, et al., *Studies in Surface Science and Catalysis*, 61, *Natural Gas Conversion*, Elsevier Science Publishers (1991), found that increased pressure decreased $C_2+$ selectivity for a strontium-doped lanthanum oxycarbonate catalyst, and recommended operating at pressures below 3 bar (43.5 psi).

It is known that some metal ions, primarily silver or copper salts, complex selectively and reversibly with olefins, and therefore they can be used to recover olefins from hydrocarbon mixtures by absorption, adsorption, or membrane separation methods. A variety of complexation agents have been developed. However, the use of complexation based separations for large-scale olefin recovery has been limited to proposals for olefin recovery in petroleum refining operations or gas-cracking olefin plants, or to purify ethylene from ethane or propylene from propane. Membranes are only suitable for small-scale recovery of olefins, such as from vent gases. Examples of such prior art complexation-based separations are disclosed in U.S. Pat. Nos. 4,174,353 and 5,859,304, and in R. B. Hall and G. R. Myers, "Effects of Product Separation on the Kinetics and Selectivity of Oxidative Coupling", pages 123–130 in M. M. Bhasin and D. W. Slocum, *Methane and Alkane Conversion Chemistry*, Plenum Press (1995), and E. M. Cordi, et al., "Steady-State Production of Olefins in High Yields During the Oxidative Coupling of Methane: Utilization of a Membrane Contactor", *Applied Catalysis A: General* 155: L1–L7 (1997).

Clearly, there is a need for improved methods for producing olefins from methane and other lower alkanes by oxidative dehydrogenation that are both economical and suitable for large-scale production. Such methods would utilize optimal reaction conditions, have few process steps, and be highly effective in recovering the olefin product, despite the olefin being present in low concentration in the reactor effluent, due to the typically low single-pass conversion that is characteristic of oxidative dehydrogenation. Such methods would avoid costly cryogenic separation of the dilute olefin products from the unconverted lower alkanes. In particular, such methods would be able to utilize the process advantages of carrying out the reaction at elevated pressure instead of at atmospheric pressure. They would also minimize the processing and disposal of reaction byproducts.

SUMMARY OF THE INVENTION

The present invention meets the above-noted objects by providing methods by which olefins, including ethylene, propylene, butenes, pentenes, hexenes and higher olefins can be produced economically and on a large-scale by the oxidative dehydrogenation of lower alkanes, i.e., methane, ethane and/or propane. The methods utilize optimal reaction conditions of elevated pressure and lower temperature, which increases catalyst stability. This is facilitated by using catalysts having performance characteristics favorable for reaction at elevated pressure. Process steps are minimized, which reduces cost and capital investment. In the case of methane, natural gas can be used as a methane source without first removing higher hydrocarbons. Byproducts such as ethane, propane, and hydrogen need not be separated from the unconverted methane or the recovered olefins. Yet the purge stream can be a small fraction of the recycle. The oxidative dehydrogenation reaction need not be integrated with other reaction steps, such as cracking byproduct ethane, which is typically run at atmospheric pressure. The olefin products are recovered selectively and efficiently from the unconverted methane, ethane, and/or propane, despite being present in low concentration, without using costly cryogenic separation. And the olefin recovery can be done at elevated pressure, thereby minimizing energy losses during decompression and compression as the gas pressure is lowered and raised, respectively. The olefin products can be readily separated with high purity.

In one embodiment, the method taught by the invention for producing olefins from one or more lower alkanes by oxidative dehydrogenation comprises the steps of: (1) supplying at least one lower alkane; (2) providing a source of oxygen; (3) converting a portion of the lower alkane by an oxidative dehydrogenation reaction process that utilizes a catalyst, to produce unconverted lower alkane containing at least one olefin product, at least one alkane byproduct, and water, wherein the reaction pressure is at least about 50 psi and olefin product(s) and alkane byproduct(s) are formed from the lower alkane with a combined selectivity of at least about 40%; (4) removing water from the unconverted lower alkane; (5) recovering the at least one olefin product from the unconverted lower alkane by using a complexation separation that utilizes at least one complexation agent to selectively remove olefins from non-olefins and which is not a membrane separation; and (6) recycling after steps (4) and (5) a majority of the unconverted lower alkane which contains the at least one alkane byproduct to the oxidative dehydrogenation reaction process of step (3).

In another embodiment, a method taught by the invention for producing ethylene and/or propylene from one or more lower alkanes by oxidative dehydrogenation comprises the steps of: (1) supplying at least one lower alkane; (2) providing a source of oxygen; (3) converting a portion of the lower alkane by an oxidative dehydrogenation reaction process that utilizes a rare earth oxycarbonate catalyst, to produce unconverted lower alkane containing at least ethylene and/or propylene, at least one alkane byproduct and/or higher olefin, and water, wherein the reaction pressure is at least about 75 psi and olefin(s) and alkane byproduct(s) are formed from the lower alkane with a combined selectivity of at least about 40% and a mole ratio of olefin(s) to alkane byproduct(s) of at least about 1/1; (4) removing water from the unconverted lower alkane; (5) recovering ethylene and/or propylene from the unconverted lower alkane by using an aqueous complexation absorption separation that utilizes at least one complexation agent containing a silver (I) ion to selectively remove ethylene and/or propylene from higher olefins and non-olefins and which is not a membrane separation; and (6) recycling after steps (4) and (5) a majority of the unconverted lower alkane which contains the at least one alkane byproduct and/or higher olefin to the oxidative dehydrogenation reaction process of step (3).

In still another embodiment, the method taught by the invention for producing olefins from one or more lower alkanes by oxidative dehydrogenation, wherein recycling of unconverted lower alkane containing reaction byproducts is reduced or eliminated, comprises the steps of: (1) supplying at least one lower alkane; (2) supplying oxygen; (3) converting a portion of the lower alkane by an oxidative dehydrogenation reaction process that utilizes a catalyst, wherein the reaction pressure is at least about 50 psi, to produce unconverted lower alkane containing at least one olefin product, at least one combustible byproduct, and water; (4) removing water from the unconverted lower alkane; (5) recovering the at least one olefin product from the unconverted lower alkane by using at least one complexation separation that utilizes a complexation agent to selectively remove olefins from non-olefins and which is not a membrane separation; and (6) adding after steps (4) and (5) a majority of the unconverted lower alkane which contains the at least one combustible byproduct to a methane gas transport system. In a preferred embodiment, the lower alkane in step (1) is processed natural gas supplied from a natural gas transport system, such as a natural gas pipeline, and the methane gas transport system of step (6) is the natural gas transport system of step (1).

In yet another embodiment, the invention is a method for manufacturing olefins from one or more lower alkanes by oxidative dehydrogenation in which a gaseous effluent having substantially the same heating value as natural gas and containing at least one reaction byproduct is added to a natural gas transport system.

DETAILED DESCRIPTION OF THE INVENTION

Figure 1:
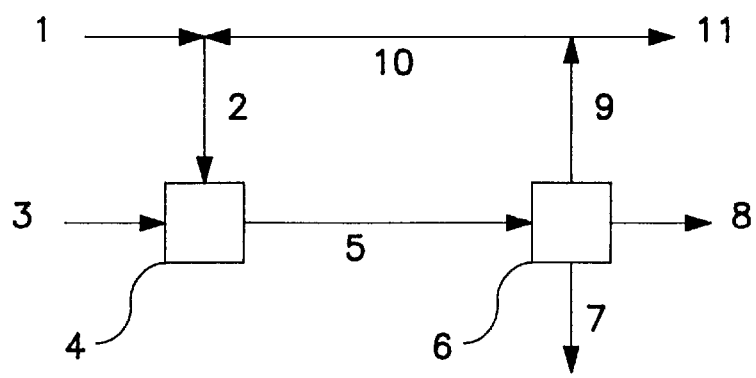
FIG. 1 is a schematic flow diagram of the recycle mode of operation of the invention.

The methods of the present invention produce olefins such as ethylene and propylene from lower alkanes by oxidative dehydrogenation. As noted above, the term "lower alkane" is understood to mean methane, ethane, and/or propane. The lower alkane is preferably methane or ethane, and is most preferably methane. Methane is a desirable raw material for making ethylene and propylene because it is less expensive and much more abundant than ethane and propane. Methane is used for producing ethylene and propylene by oxidative dehydrogenation in which a coupling reaction occurs. As used herein, the term "coupling reaction" is understood to mean a reaction in which two or more molecules are combined to form a single molecule. As also used herein, the term "oxidative dehydrogenation coupling" is understood to mean oxidative dehydrogenation in which a coupling reaction occurs. However, ethane or propane may be used as the raw material, if desired, such as to produce ethylene from ethane or to produce propylene from propane by oxidative dehydrogenation. Mixtures of the lower alkanes may also be used. Other components may also be present in the feedstock, such as inorganic gases, organic compounds and other compounds typically found in feedstocks of lower alkanes.

The methane raw material is supplied as methane gas from a methane gas source. Methane gas is any gas that contains methane, preferably with methane being the primary component. The methane gas should preferably contain at least about 70% methane by volume, more preferably at least about 80%, and most preferably at least about 90% methane. High methane content is desirable to minimize equipment size and operation cost. The methane gas may be pure or nearly pure methane if desired. The methane gas may contain ethane and propane. A methane gas source is any source of methane gas. It should be capable of supplying methane gas for large-scale production of olefins, and may be more than one source of methane gas. The primary source of methane gas is natural gas, with other suitable methane gases being refinery gas, synthetic natural gas, coal gas, and other manufactured gases and fuel gases, and gas from bacterial decomposition of biomass.

Natural gas is a mixture of naturally occurring hydrocarbon gases and inorganic gases recovered from porous geological formations by drilling wells. The composition of wellhead natural gas varies considerably among reservoirs, and the methane content may vary from below 60% to over 95% by volume. The other hydrocarbons are mainly ethane (1–15%) and progressively smaller amounts of propane, butanes, pentanes, and heavier hydrocarbons. The inorganic gases are mainly carbon dioxide, nitrogen, and hydrogen sulfide and minor to trace amounts of helium, hydrogen, argon, oxygen, organic sulfides, organic mercaptans, mercury, and other components. The gas is saturated with water vapor.

Refinery gas is a mixture of hydrocarbon gases produced in large-scale cracking and refining of petroleum. The usual components are hydrogen, methane, ethane, propane, butanes, ethylene, propylene, butenes, and perhaps nitrogen and carbon dioxide. Refinery gases include crude petroleum first distillation gas, hydroreforming gas, hydrotreatment gases, thermal cracking gas, and catalytic cracking gas. For example, an effluent gas from a catalytic cracking unit can contain 30% methane, which is separated to give a fraction containing methane, hydrogen, and nitrogen.

Synthetic natural gas is any manufactured fuel gas of approximately the same composition and heating value as natural gas. It can be produced by gasification of coal, oil shale, tar sands, petroleum, and other carbonaceous materials. Coal can be gasified to methane by reacting steam with hot coal and oxygen to form synthesis gas (carbon monoxide and hydrogen), followed by a methanation reaction. Coal gas is a mixture of methane and hydrocarbon gases produced by destructive distillation of bituminous coal or as a byproduct of coke ovens.

Wellhead natural gas typically undergoes treatment in a gas processing plant near the production field prior to its use. The acid gases, hydrogen sulfide and carbon dioxide, are removed by absorption. Hydrogen sulfide is reduced to very low levels. Carbon dioxide levels up to several percent are acceptable. Organic sulfur compounds are removed to meet mercaptan and total sulfur limits. Water is reduced to a low level. Natural gas liquids are cryogenically removed. Excessive nitrogen is typically removed since it reduces the heating value.

Conventional treatment or processing of wellhead natural gas yields treated or processed natural gas containing at least a major amount of methane and minor amounts of ethane, propane, butanes, pentanes, carbon dioxide, and nitrogen. Because wellhead gas varies widely and natural gas can be used with a wide range of hydrocarbon content, any specification for processed gas is broadly defined, and there is no universally accepted specification. Generally processed natural gas contains about 70% to more than about 95% by volume of methane, with 85% to 95% being common. The gas must contain sufficient ethane, propane, and higher hydrocarbons to compensate for the noncombustible gases in order to meet the typically required minimum gross heating value of 950 to 1000 Btu per standard cubic foot. Generally the heating value is between 1000 and 1150 Btu/scf. Typically the gas contains about 1% to 15% of ethane, with 2% to 8% being common, and progressively smaller amounts of propane and higher hydrocarbons, which total less than about 3%, with the balance being nitrogen and carbon dioxide. Component heating values are 1010 for methane, 1790 for ethane, 2520 for propane, and 3220 Btu/scf for butanes.

The lower alkane feedstock used is not critical to the methods of the present invention provided that it does not contain impurities at levels that prevent economical operation of the oxidative dehydrogenation reaction and the complexation separation of the olefin product. The lower alkane feedstock may be pretreated to remove impurities or to reduce their concentration. Undesirable impurities include sulfur compounds, materials that poison the catalyst, acetylene, and excessive levels of inert gases or higher hydrocarbons. The most preferred methane gas is processed natural gas because impurities are already at acceptable levels. The processed natural gas may be used without removing the ethane, propane, and higher hydrocarbons. However, it may be pretreated if desired.

A methane gas transport system is any system that is used to transport methane gas for large-scale use, which includes any component of such a system, such as a pipeline, tank, ship, storage facility, processing facility, pumping facility, and the like. A natural gas transport system is a methane gas transport system in which the methane gas is natural gas.

Most natural gas for large-scale use is transported from producing areas to consuming areas through extensive pipeline gathering, transmission, and distribution systems. The United States has 90,000 miles of field gathering lines, 280,000 miles of transmission lines, and 800,000 miles of distribution main lines. Of 125 pipeline systems, 47 are rated as principal pipelines. Modern gas pipelines range in diameter from 2 to 42 inches, with older pipelines being up to 56 inches. Long-distance transmission lines have diameters of 14 to 42 inches, with 36-inch pipe becoming more common. Maximum operating pressures have increased from about 500 psi for older pipelines to about 1400 psi for newer pipelines. Typical operating pressures range from about 800 to about 1000 psi. Pipeline-grade natural gas meets the specifications required by the particular pipeline system. Natural gas production and transmission systems are complemented by underground storage systems. In the United States, there are 400 storage pools supplied by about 700 gas processing plants and 260,000 producing wells.

An oxidative dehydrogenation reaction process is any reaction process that produces at least one olefin product from a lower alkane by oxidative dehydrogenation. The oxidative dehydrogenation of a lower alkane to produce olefins is carried out by contacting the lower alkane with a source of oxygen, either directly or indirectly, under reaction conditions in the presence of a catalyst.

When methane is coupled by oxidative dehydrogenation, ethylene and propylene and water are produced according to the following net reactions.

$$2\ CH_4 + O_2 \rightarrow C_2H_4 + 2\ H_2O$$

$$3\ CH_4 + 3/2\ O_2 \rightarrow C_3H_6 + 3\ H_2O$$

In addition to the desired olefin products, generally at least one alkane byproduct is produced. Ethane and propane and water are produced according to the following net reactions.

$$2\ CH_4 + 1/2\ O_2 \rightarrow C_2H_6 + H_2O$$

$$3\ CH_4 + O_2 \rightarrow C_3H_8 + 2\ H_2O$$

Higher olefins and alkanes are similarly formed in lesser amounts. In addition, secondary oxidative dehydrogenation reactions may occur, such as the following:

$$C_2H_6 + 1/2\ O_2 \rightarrow C_2H_4 + H_2O$$

$$C_3H_8 + 1/2\ O_2 \rightarrow C_3H_6 + H_2O$$

$$CH_4 + C_2H_6 + 1/2\ O_2 \rightarrow C_3H_8 + H_2O$$

When ethane is the feedstock, ethylene and water are produced by oxidative dehydrogenation according to the following net reaction.

$$C_2H_6 + 1/2\ O_2 \rightarrow C_2H_4 + H_2O$$

In addition, generally at least one alkane byproduct is produced by oxidative dehydrogenation coupling. Butane and water are produced according to the following net reaction.

$$2\ C_2H_6 + 1/2\ O_2 \rightarrow C_4H_{10} + H_2O$$

Butylene and higher olefins and alkanes are similarly formed in lesser amounts.

When propane is the feedstock, propylene and water are produced by oxidative dehydrogenation according to the following net reaction.

$$C_3H_8 + 1/2\ O_2 \rightarrow C_3H_6 + H_2O$$

In addition, generally at least one alkane byproduct is produced by oxidative dehydrogenation coupling. Hexane and water are produced according to the following net reaction.

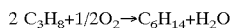

Hexylene and higher olefins and alkanes are similarly formed in lesser amounts.

The methane, ethane, propane, olefins, and alkane byproducts can undergo combustion to produce carbon monoxide, carbon dioxide, and water. Hydrogen can be produced from the carbon monoxide and water via the water-gas shift reaction, as follows.

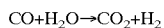

The hydrogen can also undergo combustion to water.

It is desirable to minimize production of alkane byproducts and particularly the combustion reactions, because they consume lower alkane and oxygen. Therefore, high selectivity of the lower alkane to the olefin product(s) is desired. This is increased by using a selective catalyst and desirable reaction conditions. To be economical, olefin product(s) and alkane byproduct(s) are preferably formed from the lower alkane with a combined selectivity of at least about 40%, more preferably at least about 50%, still more preferably at least about 60%, and most preferably at least about 70%. The mole ratio of olefin product(s) to alkane byproduct(s) is preferably at least about 1/1, more preferably at least about 2/1, and most preferable at least about 2.5/1.

Oxygen is generally supplied on a large scale either as high purity oxygen from an oxygen plant, as air, or as oxygen-enriched or oxygen-depleted air. Other forms and sources of oxygen commonly employed by those skilled in the art may also be used. The preferred form in which oxygen is supplied will depend upon the mode used for the oxidative dehydrogenation reaction. Air is available from the atmosphere, but air contains a large volume of inert gases, especially nitrogen, that if mixed directly with the lower alkane must pass through the reaction and product recovery systems, which increases the volumetric gas flow and equipment size, as well as being a diluent. Using air also greatly increases the cost of compressing the oxygen flow to the elevated reaction pressure. Using oxygen from an oxygen plant increases the variable cost of the raw materials, but avoids mixing nitrogen with the lower alkane, and has much less compression cost.

In the oxidative dehydrogenation reaction process, the oxygen can be contacted with the lower alkane, such as methane in methane gas, either directly or indirectly. In the cofeed mode, the lower alkane and oxygen are mixed directly together in the desired proportion and passed simultaneously over the catalyst. High-purity oxygen is preferred, but air or another oxygenated gas may be used if desired. The oxygen level in the mixture must be maintained sufficiently below the explosive limit to provide safe operation. This restricted oxygen concentration restricts the lower alkane conversion that can be obtained with a single oxygen addition. To increase the conversion level, staged oxygen addition may be used. Generally the oxygen concentration is maintained at about 10% to 13% or lower by volume. Higher oxygen concentration gives higher conversion of lower alkane, but lower reduces combustion, so the optimal concentration can depend upon the catalyst used. High oxygen conversion is favored, preferably above about 80%, more preferably above about 85%, to maximize conversion of lower alkane. Preferably the reactor does not become oxygen depleted to any significant extent. The mole ratio of lower alkane to oxygen is preferably in the range of about 4/1 to about 12/1, more preferably in the range of about 5/1 to 9/1.

In the sequential or redox mode, the lower alkane and oxygen are not directly mixed together to any substantial extent. Instead, the catalyst is an oxygen carrier and undergoes cyclic oxidation and reduction reactions as it alternately contacts the oxygen and the lower alkane. The oxygen oxidizes the catalyst so that it contains bound oxygen that is available for reaction. The lower alkane reacts with the bound oxygen and reduces the catalyst to the original lower oxidation state. The cycle is then repeated. Because the lower alkane does not contact gaseous oxygen, homogeneous oxidation is suppressed, and lower alkane conversion can safely be significantly higher than cofeed processes. An important property is the oxygen-carrying capacity of the catalyst, which is desirably as high as possible while maintaining high olefin selectivity. In this mode, air can advantageously be used as the oxygen source, because the nitrogen and other inert gases in the air are not mixed with the lower alkane. However, high-purity oxygen can also be used, which can be advantageous because compression costs are lower and equipment size can be smaller. In general, whether air or oxygen is preferred is determined by an economic analysis of the particular oxidative dehydrogenation reaction process that is used.

The sequential contacting may be done in one reactor by passing alternating flows of oxygen and lower alkane over the catalyst. An inert gas purge such as nitrogen may be passed over the catalyst in between the oxygen and lower alkane gas flows. The first purge removes free oxygen from the catalyst before it contacts the lower alkane, which eliminates uncatalyzed homogeneous reactions and improves selectivity. The second purge removes the lower alkane from the catalyst so that it is not oxidized. The purged lower alkane is recovered from the purge gas and reused. Generally the purge gas flow is minor compared to the reactant flows. Two reactors may be operated in parallel for continuous production, with one undergoing oxidation while the other undergoes oxidative dehydrogenation.

The sequential contacting is preferably done by transferring the catalyst between separate oxidation and reduction zones or reactors. This permits continuous operation and allows each reaction step to be done at optimal conditions. The catalyst is oxidized with air or oxygen in an oxidation reactor, and the oxidized catalyst is continually or periodically removed, separated from the air or oxygen, and transferred to the oxidative dehydrogenation reactor, where it is contacted with the lower alkane. The reduced catalyst is then continually or periodically removed, separated from the reaction effluent, and transferred to the oxidation reactor.

The oxidative dehydrogenation reaction process can also use other methods of contacting the lower alkane, oxygen, and catalyst. For example, using a membrane type reactor system, oxygen can be separated from air by passing it through an oxygen-transport membrane to contact the lower alkane gas and catalyst on one side of the membrane. This results in further acceleration of oxygen transport through the membrane. Other configurations of membrane reaction systems may be employed which also incorporate properly positioning the catalyst within the reactor in pill form or depositing the catalyst on the walls of the membrane reactor.

The reactor system used in the oxidative dehydrogenation reaction process is not critical to the methods of the present invention, and any suitable reactor system that operates at elevated pressure and high temperature, and which provides effective contacting of the reactants and catalyst, may be utilized. The large heat release produced by the oxidative dehydrogenation reaction and competing combustion reactions makes heat transfer and reaction temperature control important for commercial operation. The reactor design should also minimize void volume outside of the catalyst bed in order to minimize uncatalyzed gas phase reactions. Reactors particularly suited for use in the practice of the invention allow for adequate heat transfer and permit desired temperature control. Suitable reactors include tubular reactors, fluidized bed reactors, moving bed reactors, circulating fluidized bed reactors, membrane reactors, monolithic catalyst reactors, reactors containing catalyst components deposited on the reactor walls, and other reactors known to those skilled in the art. More than one reactor or more than one type of reactor may be used.

The cofeed mode of operation preferably uses a fixed-bed tubular reactor or a fluidized bed reactor. The tubular reactor provides high heat transfer surface area. Heat removal should be sufficient to promote oxygen conversion along the entire length of the reactor, so that the reaction does not occur primarily within a hot zone near the reactor entrance. Mixing in the fluidized bed reactor promotes uniform reaction temperature and good heat transfer.

The sequential mode of operation (also referred to as the cyclic mode) preferably uses a circulating fluidized bed reactor. The circulating fluidized bed reactor preferably comprises a riser reactor for the oxidative dehydrogenation reaction and a fluidized bed reactor for catalyst oxidation and regeneration. The fresh catalyst enters the riser reactor at the bottom and is carried by the rapid flow of lower alkane gas to the top of the reactor. The spent catalyst and reaction effluent are then separated, such as in a cyclone separator. The spent catalyst is then carried or flows into the top of the fluidized bed reactor or regenerator, where it is oxidized as it migrates downward through the reactor, which is fluidized by an oxygen-containing gas. The regenerated catalyst is withdrawn from the bottom of the fluidized bed, below the oxygen injection point, and is then transferred to the oxidative dehydrogenation reactor. The riser reactor can be operated adiabatically if desired with heat removal occurring in the fluidized bed reactor, such as by steam generation in internal cooling coils. This cools the heated, used catalyst to the desired oxidative dehydrogenation reactor feed temperature.

Operating gaseous reactions under pressure is generally desirable to reduce capital costs. Using elevated pressure reduces the size of process vessels and associated equipment and increases reaction rates and the efficiency of separation processes. Because the oxidative dehydrogenation reaction is not equilibrium limited, the reaction can be done at elevated pressure without limiting lower alkane conversion. Nevertheless, operating the oxidative dehydrogenation reaction, such as methane coupling, under elevated pressure has generally been avoided in the prior art, because studies have found that raising the reaction pressure significantly above atmospheric pressure produces deleterious effects that outweigh the advantages. In particular, product selectivity generally has been found to continually decrease, significantly to substantially, as the pressure is increased, due to increased homogeneous or heterogeneous combustion (on catalyst and reactor surfaces), for the catalysts tested. Other effects such as decreased lower alkane conversion and catalyst poisoning have also been reported. Contrary to these findings in the prior art, it has surprisingly been discovered that using elevated reaction pressure, as taught by the present invention, can have beneficial effects that make elevated pressure the preferred mode of operation, provided that a suitable catalyst is utilized.

Using elevated pressure provides benefits for the oxidative dehydrogenation reaction and the catalyst, and for process operation. As the reaction pressure is increased, the initiation temperature of the oxidative dehydrogenation reaction has been found to decrease substantially from the very high temperature required at atmospheric pressure. Lower reaction temperature increases catalyst stability and lifetime, and permits catalysts to be used that would become deactivated at the higher temperature. This is particularly important for catalysts that hive been discovered to have high selectivity under pressure. Lower temperature reduces reactor material of construction and heat transfer costs. Elevated pressure greatly improves heat transfer from the catalyst particles to the heat exchanger, so temperature control is improved. We have also surprisingly discovered that certain oxidative dehydrogenation catalysts have higher selectivity at elevated pressure than at atmospheric pressure, contrary to the findings in the prior art. Therefore, reaction performance can actually be improved. Because the lower alkane, such as methane gas, is usually supplied from a pipeline at high pressure, compressing the lower alkane gas to the elevated reaction pressure is not required. Elevated pressure is also beneficial to the separation method utilized in the present invention to recover the olefin product.

In the practice of the present invention, the reaction pressure should be greater than about 50 psi in order to obtain the aforementioned benefits. Preferably the reaction pressure is greater than about 75 psi, more preferably greater than about 100 psi, and most preferably greater than about 150 psi. The optimum pressure depends upon how selectivity and stability vary with pressure for the particular catalyst used. Catalysts that have high selectivity under pressure may pass through a maximum selectivity as pressure is increased, so that the selectivity can decrease to below a suitable level at excessively high pressure. Generally there is no benefit to using a reaction pressure that exceeds the elevated pressure at which the lower alkane gas is supplied from a pipeline, such as a natural gas pipeline. Otherwise the lower alkane gas must be compressed. Preferably the reaction pressure is less than about 800 psi, more preferably less than about 600 psi, and most preferably less than about 400 psi. The optimum pressure is generally determined within the range of suitable catalyst operation by an economic optimization analysis.

In the practice of the present invention, lower reaction temperature is beneficial. The reaction temperature is preferably lower than the temperature required at atmospheric pressure for the catalyst used, preferably substantially lower. The reaction temperature should be at a level that gives good catalyst performance and stability, which depends upon the pressure and catalyst used. This generally occurs about or slightly above the reaction initiation temperature required at a given pressure, preferably being less than about 100 degrees Celsius above the initiation temperature. Preferably the reaction temperature is below about 750° C., more preferably below about 700° C., still more preferably below about 650° C., and most preferably below about 600° C., although higher temperatures may be used depending on the particular catalyst employed.

In the practice of the present invention, any catalyst may be used which is effective for oxidative dehydrogenation of the lower alkane at elevated pressure. The catalyst preferably has high selectivity for olefins in accordance with the aforementioned preferred selectivities. The catalyst may be suitable for catalyzing the oxidative dehydrogenation reaction in the cofeed mode or in the sequential feed mode. When operating in the sequential feed mode, the catalyst preferably has high oxygen carrying capacity while maintaining high olefin selectivity. The catalyst particle should have suitable physical characteristics, such as particle size and abrasion resistance, for use in the reactor system utilized. Preferably the catalyst has high surface area, with higher surface area being generally more desirable. Preferably the catalyst has good stability and long lifetime.

As cofeed catalysts, many metal oxides, carbonates, and promoted mixtures, supported on substrates such as alumina, silica, and titania, have shown activity for oxidative dehydrogenation. These include alkaline earth metal oxides, alkali metal oxides or halides, and oxides of Mn, Co, Ni, Zn, Bi, Pb, Sb, Sn, Tl, In, Cd, Ge, Be, Ca, Sr, Ba, Sc, Y, Zr, La, Nd, Sm, Eu, Gd, Dy, Ho, Er, Tm, Yb, or Lu, either individually or as mixtures thereof. The metal oxides may be promoted with alkali metals or alkaline earth metals or their oxides, halides, or carbonates, either alone or as mixtures thereof. Other catalysts such as zeolites have also shown activity. Basic oxides promoted with alkali metal carbonates are important catalysts, as well as transition metal compounds.

As sequential catalysts, reducible metal oxides and other reducible compounds of the following metals have shown activity for oxidative dehydrogenation: Sn, Pb, Bi, Tl, Cd, Mn, Sb, Ge, In, Ru, Pr, Ce, Fe, Tb, Cr, Mo, Re, W, V. Promoters that may be used include oxides or compounds containing alkali metals, alkaline earth metals, boron, halogens, Cu, Zr, or Rh. The sequential catalysts may also be used as cofeed catalysts.

Suitable catalysts include promoted transition metal oxides and promoted rare earth oxides having a combined selectivity to olefin product(s) and alkane byproduct(s) of at least 40% under pressure, such as $Mn/Na_2WO_4$, $Sr/La_2O_3$, and $Sr/Sm_2O_3$.

In a preferred embodiment, the catalyst exhibits higher selectivity for olefin product(s) and alkane byproduct(s) at the reaction pressure used for oxidative dehydrogenation than the catalyst or catalyst precursor exhibits at a pressure in the range of about atmospheric pressure to about 25 psig. The higher selectivity is preferably higher by at least about 2 percentage points, more preferably by at least about 4 percentage points, and most preferably by at least about 6 percentage points. The catalyst may have lower selectivity at elevated pressure than at atmospheric pressure, provided that the selectivity remains sufficiently high for economical operation.

The catalyst preferably comprises a rare earth oxycarbonate, hydroxycarbonate, and/or carbonate catalyst. The catalyst preferably has at least one rare earth element selected from the group consisting of La, Pr, Nd, Sm, Eu, Gd, Th, Dy, Ho, Er, and Tm. The catalyst may further comprise a cocatalyst containing at least one metal selected from the group consisting of V, Nb, Ta, Cr, Mo, W, Mn, Re, Fe, Co, Ni, Cu, Zn, Sn, Pb, Sb, and Bi. The catalyst or cocatalyst may also contain at least one alkali metal or alkaline earth metal.

The catalyst composition in the reactor is typically uniform. However, for fixed beds, more than one composition can be employed in a stacked bed or graded bed configuration to take advantage of coupling and dehydrogenation functions of such catalysts.

In a preferred embodiment, the catalyst is capable of oxidatively dehydrogenating the at least one alkane byproduct to form at least one olefin, such as oxidatively dehydrogenating ethane to form ethylene; propane to form propylene; butane to form butylene; etc. This is highly desirable to increase the olefin yield by utilizing the recycled alkane byproduct.

In a preferred embodiment, the catalyst is a rare earth oxycarbonate catalyst. The catalyst preferably comprises a nonstoichiometric rare earth oxycarbonate of the formula $M_xC_yO_z$ which has a disordered and/or defect structure, wherein M is at least one rare earth element selected from the group consisting of La, Pr, Nd, Sm, Eu, Gd, Tb, Dy, Ho, Er, and Tm; X=2; Z=3+AY; A is less than about 1.8; and Y is the number of carbon atoms in the oxycarbonate, and said catalyst, when used for the oxidative dehydrogenation of said lower alkane at a pressure above about 100 psig, has a selectivity of at least about 40% to olefin product(s) and alkane byproduct(s). The catalyst may further comprise a cocatalyst containing at least one metal selected from the group consisting of V, Nb, Ta, Cr, Mo, W, Mn, Re, Fe, Co, Ni, Cu, Zn, Sn, Pb, Sb, and Bi. The catalyst or cocatalyst may also contain at least one alkali metal or alkaline earth metal. The catalyst may also contain a support material, which preferably has a formed shape. The catalyst preferably has a surface area greater than about 20 $m^2/g$. We have discovered that such catalysts give high selectivity at elevated pressure, have low reaction temperature, and have good catalyst stability and long lifetime. Such catalysts can also exhibit higher selectivity for olefin product(s) and alkane byproduct(s) at elevated pressure than at atmospheric pressure.

The nonstoichiometric rare earth oxycarbonate catalyst may be prepared by (1) forming a catalyst precursor from at least one rare earth compound including at least one rare earth element selected from the group consisting of La, Pr, Nd, Sm, Eu, Gd, Tb, Dy, Ho, Er, and Tm and oxygen, by treating the at least one rare earth compound with water and/or an organic compound that contains a hydroxyl group, drying the treated rare earth compound, and calcining the treated rare earth compound at a temperature in the range of about 300° C. to about 1000° C. in an atmosphere containing oxygen; and (2) forming said catalyst by (a) pressurizing the catalyst precursor to a pressure of at least about 100 psig with a flowing gas including at least one hydrocarbon and oxygen, and (b) heating the catalyst precursor and holding the catalyst precursor for at least about 20 minutes at one or more temperatures within the temperature range of about 300° C. to about 600° C. wherein oxygen conversion is below about 70%. The rare earth compound may be selected from the group consisting of rare earth oxides, hydroxides, acetates, carbonates, and nitrates. At least one cocatalyst compound containing at least one metal selected from the group consisting of V, Nb, Ta, Cr, Mo, W, Mn, Re, Fe, Co, Ni, Cu, Zn, Sn, Pb, Sb, and Bi may be added to the rare earth compound and/or the catalyst precursor.

The nonstoichiometric rare earth oxycarbonate catalyst may also be prepared by (1) treating at least one finely divided solid rare earth compound comprising at least one rare earth element selected from the group consisting of La, Pr, Nd, Sm, Eu, Gd, Tb, Dy, Ho, Er, and Tm and oxygen with water and an organic acid to form an aqueous mixture such that the final pH of the aqueous mixture has a substantially constant value in the range of about 2 to about 6; (2) drying the aqueous mixture to a substantially dry state such that the treated rare earth compound does not form a foamed material; and (3) calcining the treated rare earth compound in a flowing atmosphere containing oxygen at a temperature in the range of about 300° C. to about 600° C. to provide a nonstoichiometric rare earth oxycarbonate catalyst. A preferred rare earth compound is a rare earth oxide, such as lanthanum oxide. The organic acid may be acetic acid, formic acid, propionic acid, or butyric acid, preferably acetic acid. At least one cocatalyst compound containing at least one metal selected from the group consisting of V, Nb, Ta, Cr, Mo, W, Mn, Re, Fe, Co, Ni, Cu, Zn, Sn, Pb, Sb, and Bi may be added to the rare earth compound.

Suitable catalysts for use in the invention are further described in commonly owned, patent application entitled "Catalysts for the Oxidative Dehydrogenation of Hydrocarbons", Ser. No. 04/664,954 filed on even date herewith now U.S. Pat. No. 6,403,523, the disclosure of which is incorporated herein by reference.

The oxidative dehydrogenation reaction process converts a portion of the lower alkane to produce unconverted lower alkane containing at least one olefin product, at least one alkane byproduct, and water. The unconverted lower alkane in addition may contain carbon dioxide and carbon monoxide from combustion as well as hydrogen, unreacted oxygen, and perhaps other components, such as diluent nitrogen and inert gases. The conversion of lower alkane achieved depends upon the mode of operation, the catalyst used, and the reaction conditions. In the cofeed mode, the conversion of lower alkane is generally less than about 30%, more typically about 20% or less, due to safety limits on the oxygen level. In the sequential mode, the conversion of lower alkane can be higher, but generally it is less than about 80%, more typically about 40% or less. The reaction is also generally operated with limited conversion because product selectivity typically declines at high conversion, because the product undergoes oxidation to a greater extent. Therefore the olefin product must be recovered from a large amount of unconverted lower alkane that also contains a mixture of other components. Therefore it is highly desirable to utilize a separation method that selectively and efficiently recovers the olefin product from the unconverted lower alkane. The present invention utilizes such a separation method, which is superior to those utilized in the prior art.

In the present invention, the at least one olefin product is recovered from the unconverted lower alkane by using a complexation separation to selectively remove olefins from non-olefins and which is not a membrane separation. Any complexation separation may be used provided that it is capable of selectively separating olefins with high recovery and on a large scale from the unconverted lower alkane. The separation method is preferably an absorption or adsorption complexation separation, most preferably an absorption complexation separation.

A complexation separation of olefins uses a complexing agent to selectively form a reversible complex with the olefins.

Olefin+Complexing Agent⇌Olefin-Agent Complex

Reversibility of the complexation reaction allows the olefin to be captured and released by shifting the direction of the reaction equilibrium. The forward complexation reaction is favored by higher olefin partial pressure and lower temperature, whereas the reverse desorption reaction is favored by lower olefin partial pressure and higher temperature. Therefore a complexation/desorption cycle can be generated by swinging the pressure, the temperature, or both. Because non-olefins are not complexed by the complexing agent, the olefins are selectively complexed and removed from the unconverted lower alkane gas, and then they are desorbed and recovered with high purity after the gas has been removed. The complexation separation preferably utilizes a π-bond complex to selectively remove olefins from non-olefins.

The complexing agent should selectively and reversibly form a complex with olefins, complex minimally with non-olefins, and be subject to minimal irreversible poisoning by impurities so that it has good stability and long lifetime. The complexing agent should be able to complex the olefins with high loading in order to reduce equipment size. The complexation and desorption reaction kinetics should be sufficiently rapid that complexation and desorption times are sufficiently short for economical operation. Any complexing agent or mixture of complexing agents that meets these requirements may be used in the practice of the present invention.

The complexing agent may be in the form of a metal salt or a metal complex, or another type of complexing agent may be used. Salts or compounds of silver (I) or copper (I), either by themselves or combined with another metal, such as aluminum, are the most common complexing agents that have been developed for olefin separation, but other materials are also known, such as derivatized molybdenum sulfide. The complexation agent preferably contains a silver (I) ion or a copper (I) ion, most preferably a silver (I) ion.

In an adsorption separation, the olefins are preferentially adsorbed onto a solid complexing adsorbent that contains the complexing agent. A number of solid adsorbents have been developed, such as silver or copper ion-exchanged zeolites and cation exchange resins; polystyrene-supported aluminum silver chloride; copper halide on activated carbon, silica gel, γ-alumina, or macroreticular polystyrene containing amino groups; solid anhydrous silver hexafluorophosphate; and solid porous silver salts, such as silver nitrate. The adsorbent should give high olefin loading and have high surface area, favorably rapid adsorption and desorption kinetics, and good mechanical stability. Pressure-swing methods are preferred to temperature-swing methods.

In an absorption separation, the olefins are preferentially absorbed into a complexing solution that contains the complexing agent dissolved in a solvent. A number of soluble complexing agents have been developed, which are mainly silver (I) or copper (I) salts. Suitable silver absorbents include silver nitrate, silver fluoborate, silver fluosilicate, silver hydroxyfluoroborate, and silver trifluoroacetate. Suitable copper absorbents include cuprous nitrate; cuprous halides such as cuprous chloride; cuprous sulfate; cuprous sulfonate; cuprous carboxylates; cuprous salts of fluorocarboxylic acids, such as cuprous trifluoroacetate and cuprous perfluoroacetate; cuprous fluorinated acetylacetonate; cuprous hexafluoroacetylacetonate; cuprous dodecylbenzenesulfonate; copper-aluminum halides, such as cuprous aluminum tetrachloride; $CuAlCH_3Cl_3$; $CuAlC_2H_5Cl_3$; and cuprous aluminum cyanotrichloride. Because the unconverted lower alkane generally contains water vapor, unless dried prior to the separation, the absorbent is preferably stable to hydrolysis. The complexing agent preferably is stable and has high solubility in the solvent.

For producing highly pure ethylene and propylene while minimizing the separation steps required, preferably the complexation agent selectively absorbs ethylene and propylene, but does not absorb higher olefins such as butenes and pentenes to any significant extent. Then the recovered olefin contains just ethylene and propylene, which can be separated by distillation without having to also separate the higher olefins. Preferably the complexation agent recovers a mixture of ethylene and propylene that contains less than about 1% by weight of higher olefins.

Copper is much less expensive than silver, so the absorbent inventory cost can be much lower, and copper is much less affected by hydrogen than silver, but there are several performance differences that favor silver over copper. Copper salts have lower solubility and provide a substantially lower ethylene loading capacity, so solution circulation rates are much higher. Copper solutions have a greater affinity for carbon monoxide relative to ethylene than silver solutions, and the carbon monoxide is not removed by stripping. Copper (I) is not a completely stable oxidation state, and it is readily oxidized to copper (II) or reduced to copper metal, neither of which complexes with olefins. Silver (I) salts are stable in aqueous solution, are insensitive to oxidation, and do not disproportionate to form metallic silver. For these reasons, silver (I) salts are the preferred absorption complexing agent. Complexation agents that contain silver (I) ion have furthermore been discovered in the present invention to be able to selectively absorb ethylene and propylene, but to not absorb higher olefins such as butenes and pentenes to any significant extent. Optionally, a mixture of complexing agents may be employed, e.g., a mixture of copper and silver salts.

Any suitable solvent or mixture of solvents may be used to dissolve the complexing agent. The solvent preferably is stable, dissolves the complexing agent in high concentration, has low vapor pressure, and promotes separation of olefins from non-olefins. Water is commonly used as a solvent for inorganic silver or copper salts whereas hydrocarbon solvents, such as aromatic solvents, are used for salts that contain organic ligands. Water is the preferred solvent because lower alkanes and alkane byproducts, such as ethane and propane, and other non-olefins such as nitrogen are exceedingly sparingly soluble in aqueous solutions under pressure, particularly at high salt concentrations. In contrast, alkane byproducts have high solubility in hydrocarbon solvents. Olefins have sufficient solubility in water for mass transfer to the dissolved complexing agent to occur at a reasonable rate.

A modifier or mixture of modifiers, such as an acid, a salt that does not complex olefins, an oxidizing agent, or a functional organic compound, may be used to increase the solubility and/or stability of the complexing agent in the solvent.

Aqueous silver nitrate is the most preferred complexing agent in the practice of the present invention. Aqueous silver nitrate has high solubility, is very stable, and any elemental silver that should be formed can readily be redissolved by using a small amount of nitric acid. The silver nitrate is preferably present in the solution at a high concentration that is stable to reduction in order to maximize olefin loading capacity. This is generally obtained with silver nitrate concentrations in the range of about 3 molar to about 8 molar, more preferably from about 4 molar to about 6 molar. Silver nitrate solubility is 10.9 molar (75.4% by weight) at 35° C. Silver nitrate can be used to recover an ethylene and propylene mixture in high purity because the small amount of butenes and higher olefins that are produced by oxidative dehydrogenation are not absorbed by the silver nitrate. The silver nitrate may be used with other complexation agents if desired. Ethylene absorption and other data for aqueous silver nitrate is given in G. E. Keller, et al., "Olefin Recovery and Purification via Silver Complexation", Chapter 3 in N. N. Li, et al., *Separation and Purification Technology,* Marcel Dekker (1992).

There are a few materials that are desirably not present in the feed to the complexation separation because they can react adversely with the complexing agent. Oxygen should be excluded from copper systems to avoid oxidizing copper (I) to copper (II). Both silver and copper react irreversibly with many sulfur compounds, so sulfur should be reduced to very low levels. Failure to remove hydrogen sulfide causes silver or copper loss by formation of a sulfide, which would eventually deactivate the solution. Because sulfur can poison the catalyst, generally sulfur has already been reduced to an acceptably low level in the lower alkane gas feed. Halogenated compounds, such as a chloride promoter for the oxidative dehydrogenation reaction, should also be avoided. Oxygenated organic compounds are generally avoided as well.

Another difficulty arises from acetylinic hydrocarbons, particularly acetylene and methyl acetylene. Acetylenes that contain an active hydrogen form silver or copper acetylide compounds that have limited solubility in aqueous solution and do not decompose during desorption, so they can accumulate until they precipitate. This consumes absorbent, interferes with flow, and generates a safety hazard. These precipitates are susceptible to detonation, especially when dry, so precautions must be taken to deal with them effectively. However, unlike thermal cracking processes, acetylene has not been seen as a byproduct of the oxidative dehydrogenation reaction. If necessary, acetylene can be removed by selective hydrogenation or by an absorption process that uses acetone or a dimethylformamide.

Silver acetylide concentration from trace levels of acetylene can be maintained at a safe level by using silver permanganate as an oxidant. A small sidestream is withdrawn from the desorber and heated to about 75° C. under partial vacuum. Solid silver permanganate is added to destroy the acetylide, which forms carbon dioxide and free silver ion. The resulting manganese dioxide precipitates and is filtered from solution. This recovers silver without adding a foreign ion. Data and treatment of silver acetylides are given in U.S. Pat. No. 4,174,353.

Hydrogen can cause a gradual reduction to metallic silver, but hydrogen need not be removed from the feed. Oxidative dehydrogenation produces much less hydrogen than thermal cracking. However, silver reduction must be eliminated to prevent silver from being continually lost by forming colloidal particles and by plating out on surfaces. The addition of small amounts of hydrogen peroxide coupled with a maintenance level of nitric acid in the solution stabilizes the dissolved silver against precipitation. A synergistic effect occurs because much more hydrogen peroxide is necessary if nitric acid is not present. More information is given in U.S. Pat. No. 4,174,353. The hydrogen peroxide causes in situ oxidation of a small amount of olefin to carbon oxides. At typical conditions of 0.35% hydrogen peroxide and 0.5% nitric acid by weight, the recovered olefin contains about 30 ppm carbon monoxide and 75 ppm carbon dioxide, as well as about 60 ppm of oxygen from the breakdown of the hydrogen peroxide, and water vapor from the aqueous solution. These contaminants can be removed, if necessary, by simple scavenging treatments. For example, carbon monoxide and oxygen can be easily removed by copper oxide and metallic copper oxidation, respectively, carbon dioxide by a caustic wash, and water by molecular sieves.

Aqueous silver solutions are stable in the presence of lower alkanes, alkane byproducts, carbon monoxide, carbon dioxide, oxygen, nitrogen, and other inert gases. However, these gases have a small but finite solubility in aqueous solutions, so small amounts are physically absorbed into the solution along with the complexed olefins. Therefore, the absorption separation generally has three main steps: absorption of the olefins into the solution, venting off of the non-olefin impurities from the solution, and desorption of the recovered olefins from the solution.

The absorption of the olefins is carried out under pressure and at low temperature in a countercurrent-flow absorber column. Packing is preferred instead of trays to minimize the inventory of silver solution. A high silver concentration maximizes olefin uptake and minimizes equipment size and circulation rate. Olefin absorption is increased by higher pressure. The pressure is generally at least about as high as the reaction pressure, and it may be increased by compressing the feed of unconverted lower alkane. The pressure is preferably above about 100 psi, more preferably above about 200 psi. Generally the absorber pressure does not exceed pressures typical of natural gas pipelines. Olefin absorption is increased by lower temperature, which stabilizes the complex. The absorber solution feed temperature is preferably below about 50° C., more preferably below about 40° C., and most preferably from about ambient temperature to about 35° C. Subambient temperature may be used if desired, but refrigeration increases cost. The absorption is exothermic, which heats the solution and decreases the olefin loading. Therefore an excessive temperature rise should be avoided, and internal cooling may be used if desired. The optimum pressure and temperature are generally determined as optimization variables of an economic analysis. The olefin recovery from the unconverted lower alkane in the absorption column is preferably above 95%, more preferably above 98%.

The absorbed impurities are vented from the solution in a vent column before the olefins are desorbed. The vent column operates at a pressure that is intermediate between the absorption pressure and atmospheric pressure, so that the impurities are purged but the olefin remains absorbed. The impurities are purged by flashing and by feeding a small fraction of the recovered olefin to the bottom of the column as a purge gas. The resulting purge stream is compressed and added to the absorber feed. A lower operating pressure for the vent column reduces the stripping gas flowrate but increases the amount of olefin that is recycled back to the absorber for recovery. After passing through the vent column, the solution contains absorbed olefin at or near high purity.

Before entering the desorber column, the solution is flashed to atmospheric pressure in one or more stages. The flashed olefin is separated in the flash vessel and added to the olefin product recovered from the desorber column. If the flash is staged, the olefin fractions may be added, at their intermediate pressures, to the stages of an olefin compressor that compresses the crude recovered olefin to refining pressure.

The flashed solution is heated and fed to the top of the desorber column, which operates at about atmospheric pressure or preferably at sub-atmospheric pressure, such as from about 7 psia to about 10 psia, to better strip the olefin from the solution. A lower operating pressure reduces energy consumption but increases the compression requirements of the olefin gas compressor. The feed solution is preferably heated to a temperature in the range of about 55° C. at about 90° C., preferably from about 65° C. to about 80° C. The olefin recovery from the solution should be very high, preferably above about 95%, more preferably about 98% or higher, to minimize olefin loss in the absorber overhead gas. The stripped solution is then cooled and recycled to the absorber column.

The recovered crude olefin is compressed, treated to remove residual impurities, and refined by cryogenic distillation to separate the olefin fractions and to produce pure olefin products. The at least one olefin product may subsequently be converted into at least one olefin derivative, wherein the production rate of the at least one olefin is substantially the same as the supply rate, of the at least one olefin, that is required to manufacture the at least one olefin derivative at a desired production rate. Suitable olefin derivatives include polyolefin, ethylene-propylene rubber, ethylene oxide, ethylene glycol, ethanol, and hydrocarbon fuel.

The present invention may be operated in a recycle mode or a single-pass mode with respect to the flow of unconverted lower alkane. from the oxidative dehydrogenation reaction process after the olefin product has been removed by the complexation separation.

The recycle mode of operation is illustrated by the flow diagram in FIG. 1. Lower alkane gas feed (1) is added to recycled unconverted lower alkane (10) and the resulting mixture (2) and the oxygen feed (3) are supplied to the oxidative dehydrogenation reaction process (4), which produces an effluent of unconverted lower alkane (5) containing at least one olefin product, at least one alkane byproduct, and water. The unconverted lower alkane (5) is then processed by a product recovery operation (6) to remove water (7), such as by condensation, and to recover the at least one olefin product (8) by using a complexation separation. The product recovery operation produces an effluent of unconverted lower alkane (9) that contains the at least one alkane byproduct. A portion of the unconverted lower alkane is desirably taken as a purge (11). A majority of the unconverted lower alkane (10) which contains the at least one alkane byproduct is then recycled to the oxidative dehydrogenation reaction process. Alternatively, the lower alkane gas feed and the recycled unconverted lower alkane may be added separately to the oxidative dehydrogenation reaction process. The water may be removed before and/or after the complexation separation.

We have unexpectedly discovered that when the oxidative dehydrogenation reaction is done at elevated pressure, the at least one alkane byproduct can be beneficially recycled to the reaction, so it does not have to be recovered from the recycled unconverted lower alkane to avoid undesirable combustion. We have found that a majority of the alkane is instead oxidatively dehydrogenated to olefin, which beneficially increases the overall olefin yield. For the same reason, alkanes need not be removed from a methane gas feed. This greatly simplifies the process and reduces cost. A detailed kinetic study indicates that ethane can be converted to ethylene with a high selectivity of about 70% or higher and with high conversion. The remaining ethane undergoes combustion primarily to carbon dioxide and a minor amount of carbon monoxide. This relationship was found to occur independently of the ethane concentration in the reactor feed. Therefore a large purge rate is not required to keep the alkane byproduct at an acceptable low level. The alkane byproduct concentration in the recycled unconverted lower alkane is preferably less than about 20% by weight, more preferably less than about 10%.

The unconverted lower alkane in addition to the olefin product and alkane byproduct may contain carbon dioxide, carbon monoxide, hydrogen, unreacted oxygen, nitrogen, and other compounds. The carbon monoxide and hydrogen when recycled undergo combustion to carbon dioxide and water, respectively, so they need not be removed from the unconverted lower alkane. Similarly, higher olefins and alkanes, such as butenes and butanes, are recycled to extinction by combustion. The concentration of nitrogen and other inert compounds that enter with the feed materials are controlled by the purge rate. One benefit of the recycle mode of operation is that the oxidative dehydrogenation reaction can be operated with less than total oxygen conversion, which reduces reactor size. The unreacted oxygen is recycled with the unconverted lower alkane.

Although the carbon dioxide concentration can be controlled by the purge rate, preferably at least a portion of the carbon dioxide is removed from the recycled unconverted lower alkane, such as by absorption, so that it does not accumulate to a high level for the oxidative dehydrogenation reaction. Preferably the carbon dioxide concentration in the lower alkane feed to the oxidative dehydrogenation reaction process is below about 25% by weight, still more preferably below about 15%, and most preferably below about 5%. The carbon dioxide may be removed before or after the complexation separation, preferably after.

We have discovered that the recycle mode of operation can be operated with a much smaller purge rate than had been anticipated. Although higher purge rates may be used, the purge rate is preferably less than about 10% of the flow of recycled unconverted lower alkane, more preferably less than about 5%, and most preferably less than about 3%. The purge rate will depend upon the particular catalyst and operating conditions that are used. Because in large-scale production the recycle flow rate can be very large, even a small fractional purge rate can produce a large flow of unconverted lower alkane gas. Therefore, instead of utilizing the purge directly as a fuel gas, a purge of the unconverted lower alkane which contains the at least one alkane byproduct may be added to a methane gas transport system, such as a natural gas pipeline. If necessary, the purge may be treated to adjust the fuel value to that of the methane gas transport system. The purge may also be treated to remove residual oxygen content. This allows larger purges to be used economically than would otherwise be possible.

Figure 2:
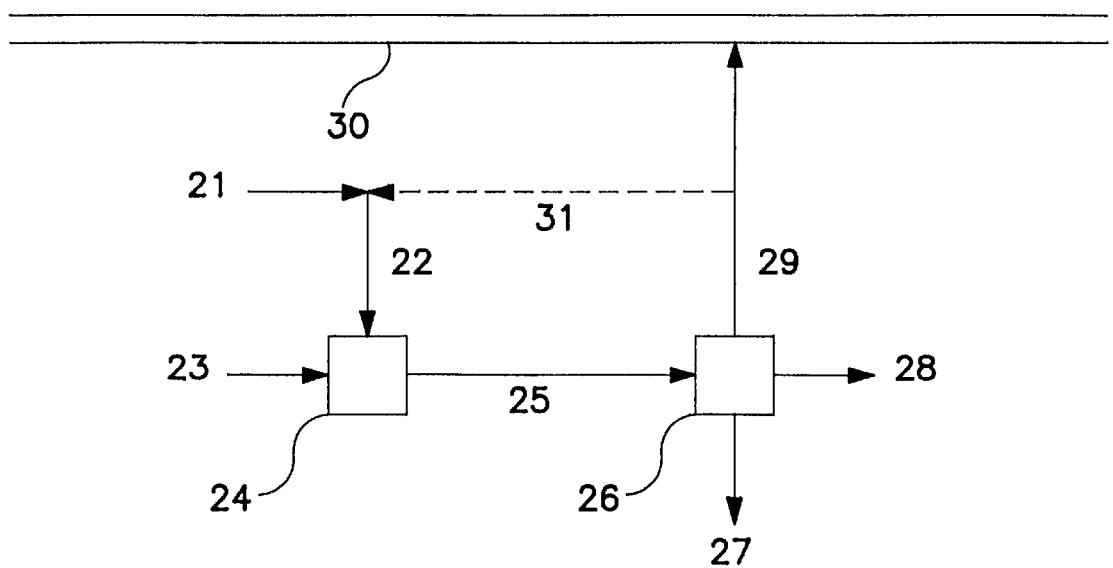
FIG. 2 is a schematic flow diagram of the single-pass mode of operation of the invention.

The single-pass mode of operation is illustrated by the flow diagram in FIG. 2. Lower alkane gas feed (21) is added to optional recycled unconverted lower alkane (31) and the resulting mixture (22) and the oxygen feed (23) are supplied to the oxidative dehydrogenation reaction process (24), which produces an effluent of unconverted lower alkane (25) containing at least one olefin product, at least one combustible byproduct, and water. The unconverted lower alkane (25) is then processed by a product recovery operation (26) to remove water (27) and to recover the at least one olefin product (28) by using a complexation separation. The product recovery operation produces an effluent of unconverted lower alkane (29) that contains the at least one combustible byproduct. A majority of the unconverted lower alkane (29) which contains the at least one combustible byproduct is then added to a methane gas transport system. If desired, a minority of the unconverted lower alkane may optionally be recycled (31) to the oxidative dehydrogenation reaction process. A portion of the unconverted lower alkane may also optionally be taken as a purge (not shown). Alternatively, the lower alkane gas feed and the recycled unconverted lower alkane may be added separately to the oxidative dehydrogenation reaction process. The water may be removed before and/or after the complexation separation. The water content of the unconverted lower alkane is preferably reduced to a low level before the unconverted lower alkane is added to the methane gas transport system. Most of the water can be readily removed by condensation and the remainder reduced to a low level by using molecular sieve adsorbent.

By using the single-pass mode of operation, recycling of unconverted lower alkane containing reaction byproducts can be reduced or preferably eliminated, while avoiding having to separate the byproducts from the lower alkane in order to derive an economical benefit from the large amount of unconverted lower alkane. Preferably at least about 60% of the unconverted lower alkane is added to the methane gas transport system, more preferably at least about 80%, still more preferably at least about 90%, and most preferably at least about 95%. The methane gas transport system desirably has a substantially larger flow of methane gas than the flow of added unconverted lower alkane, preferably at least about twice as large, more preferably at least about three times as large, still more preferably at least about five times as large, and most preferably at least about ten times as large.

In the practice of the present invention, the source of the lower alkane used for the lower alkane gas feed is not critical, and it either may or may not be the methane gas transport system to which the unconverted lower alkane is added. In a preferred mode of operation, the at least one lower alkane supplied to the oxidative dehydrogenation reaction process is processed natural gas supplied from a natural gas transport system, and the unconverted methane is added to the same natural gas transport system. This ensures that unacceptable impurities are not introduced from the feed source. The natural gas transport system is preferably a natural gas pipeline, and the unconverted methane is preferably added to the pipeline downstream from where the natural gas feed is withdrawn from the pipeline.

The oxygen supplied to the oxidative dehydrogenation reaction process is preferably high purity oxygen instead of air, to avoid adding nitrogen and other noncombustible gases from air to the methane gas transport system. The oxygen content of the unconverted lower alkane is preferably reduced to a low level by running the oxidative dehydrogenation reaction at nearly complete oxygen conversion or by reacting the residual unconverted oxygen in some other manner. This can be done by passing the reaction effluent through a converter in which the carbon monoxide byproduct is oxidized to carbon dioxide and the remaining oxygen is hydrogenated by the hydrogen to water.

The unconverted lower alkane is preferably compressed prior to the complexation separation to about the pressure of the methane gas transport system to which it is added, to improve absorption of the olefin product.

Compared to the recycle mode, the single-pass mode produces a lower concentration of reaction byproducts in the unconverted lower alkane. This is particularly true for hydrogen, carbon dioxide, and carbon monoxide. The lower hydrogen level is beneficial to the stability of silver nitrate in the complexation separation. A lower level of recycled byproducts can be beneficial to some catalysts. Although not required, at least a portion of the carbon dioxide may be removed before the unconverted lower alkane is added to the methane gas transport system, to increase the fuel value. If necessary, the unconverted lower alkane may be further treated to remove impurities or to further adjust the fuel value to that of the methane gas transport system.

When the lower alkane is ethane or propane, the recycle mode of operation is preferred to the single-pass mode of operation, because ethane and propane are more expensive than methane or natural gas, so it is less cost effective to recover fuel value for the unconverted ethane or propane by adding it to a methane gas transport system.

EXAMPLE 1

Figure 3:
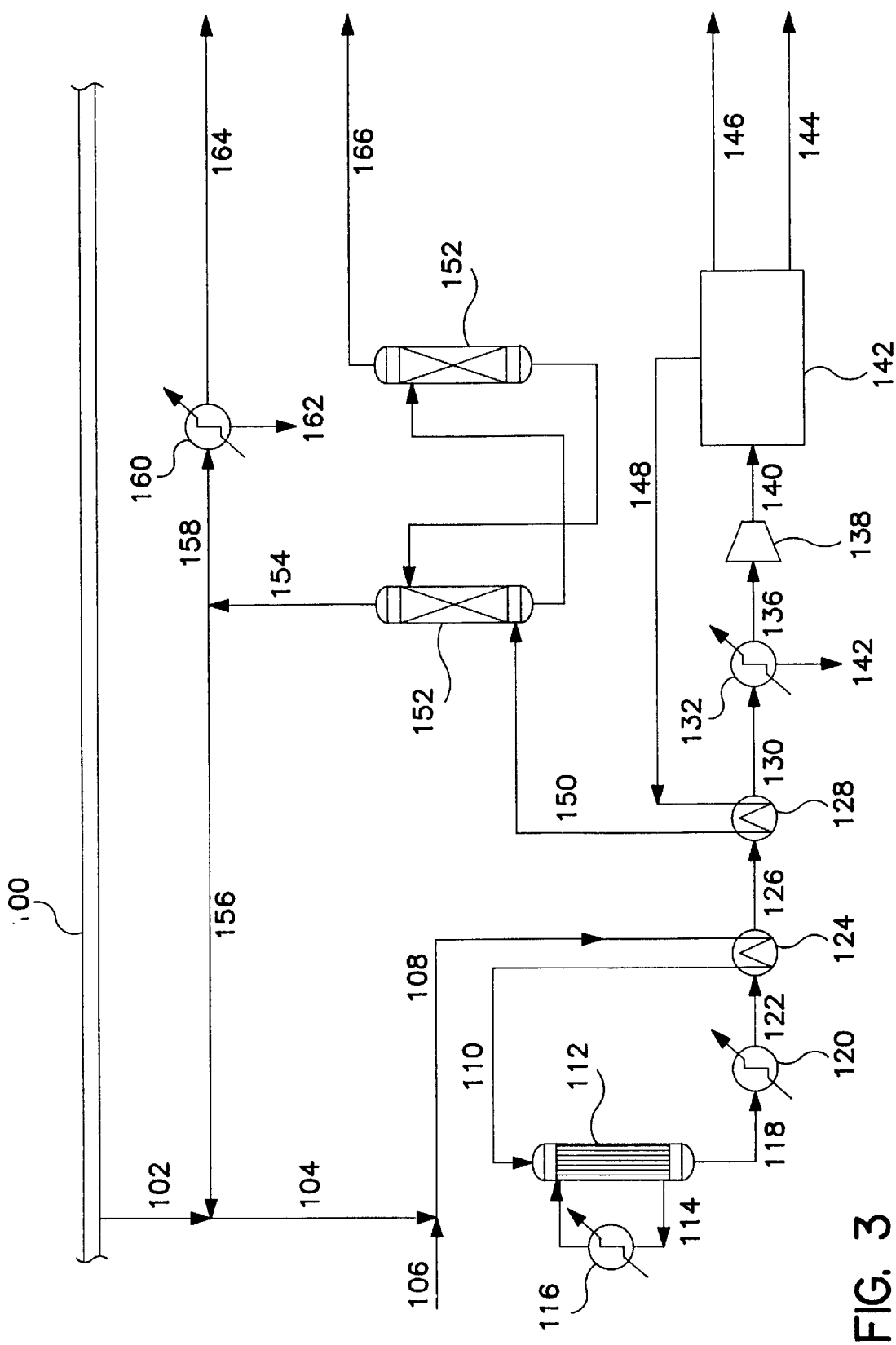
FIG. 3 is a process flow diagram illustrating an example of the recycle mode of operation of the invention.

An example of the recycle mode of operation is given by the process flow diagram in FIG. 3. In this example, the primary lower alkane is methane gas. Similar process flow diagrams can be derived for ethane or propane being the lower alkane by one skilled in the art by using the principles and guidelines illustrated. The methane gas (102) is processed natural gas from a natural gas pipeline (100) that has a pressure of 825 psia and contains 1.0% ethane, 0.04% propane, 0.30% nitrogen, and 0.56% carbon dioxide. The methane gas is expanded down to 260 psia and 18° C. and then combined with recycled unconverted methane gas (156) that contains ethane, propane, and other byproducts at 108° C. The combined flow (104) is mixed with high purity oxygen (106) and the resulting cofeed gas mixture (108) at 88° C. is preheated to 250° C. by the hot reaction product (122) in heat exchanger 124 and fed (110) to two fixed bed catalytic reactors (112) operating in parallel. The reactor feed contains 60.8% methane, 21.2% oxygen, 2.5% ethane, 0.2% propane, 4.5% water, 4.4% carbon dioxide, 1.2% carbon monoxide, 0.7% hydrogen, 4.3% nitrogen, and trace amounts of ethylene, propylene, butene, and butane, by weight. The mole ratio of methane to oxygen is 5.7 and the oxygen concentration is 12% by volume. The oxidative dehydrogenation reaction temperature is maintained at about 540° C. by circulating molten salts (114) through the reactors. The salts (HITEC) are cooled in cooler 116 by generating 600 psig steam, which is consumed elsewhere in the process in steam turbines and column reboilers. Because there is no restriction on the allowable oxygen conversion in the recycle mode of operation, the oxygen conversion has been optimized at 90%. The methane conversion is 20%, with 80% selectivity to ethylene and ethane in a mole ratio of 3/1, 8% selectivity to propylene and propane in a ratio of 5/1, 1% selectivity to 1-butene and n-butane in a ratio of 7/1, and 11% selectivity to carbon dioxide and carbon monoxide in a ratio of 11.5/1. The hot reactor product (118) at 215 psia is cooled to 300° C. by generating 600 psig steam in heat exchanger 120 and cooled to 149° C. by the cold reactor feed (108) in heat exchanger 124. The crude reaction product gas (126) is cooled to 127° C. (130) in heat exchanger 128 by the cold vent stream (148) leaving the silver complexation absorption system (142) and is finally cooled to 40° C. (136) in cycle gas cooler 132, which removes most of the water (134) by condensation. The cooled reaction product (136) is compressed by compressor 138 from 190 psia to 275 psia (140) and sent to the silver complexation absorption system (142), which will be described separately, in which ethylene (146) and propylene (144) are recovered selectively by complexation with a circulating silver nitrate solution. The unconverted methane gas (148) from this system at 35° C. is preheated to 93° C. (150) in heat exchanger 128 before entering a Benfield hot potassium carbonate unit (152) to remove a portion of the carbon dioxide (166). Because there is no restriction on the carbon dioxide concentration in the fuel gas purge, the fraction of carbon dioxide removed has been optimized at 60%. The unconverted methane (154) leaves the carbon dioxide absorber at 108° C. A purge (158) of 2.0% of the unconverted methane is taken from the recycle to remove inerts such as nitrogen and reaction byproducts. The purge is cooled by cooler 160 to remove water (162) to produce the final purge stream (164). The purge is small enough to be consumed by a gas-fired steam boiler. The remaining unconverted methane (156) containing ethane, propane, and other byproducts is recycled to the oxidative dehydrogenation reaction.

Figure 4:
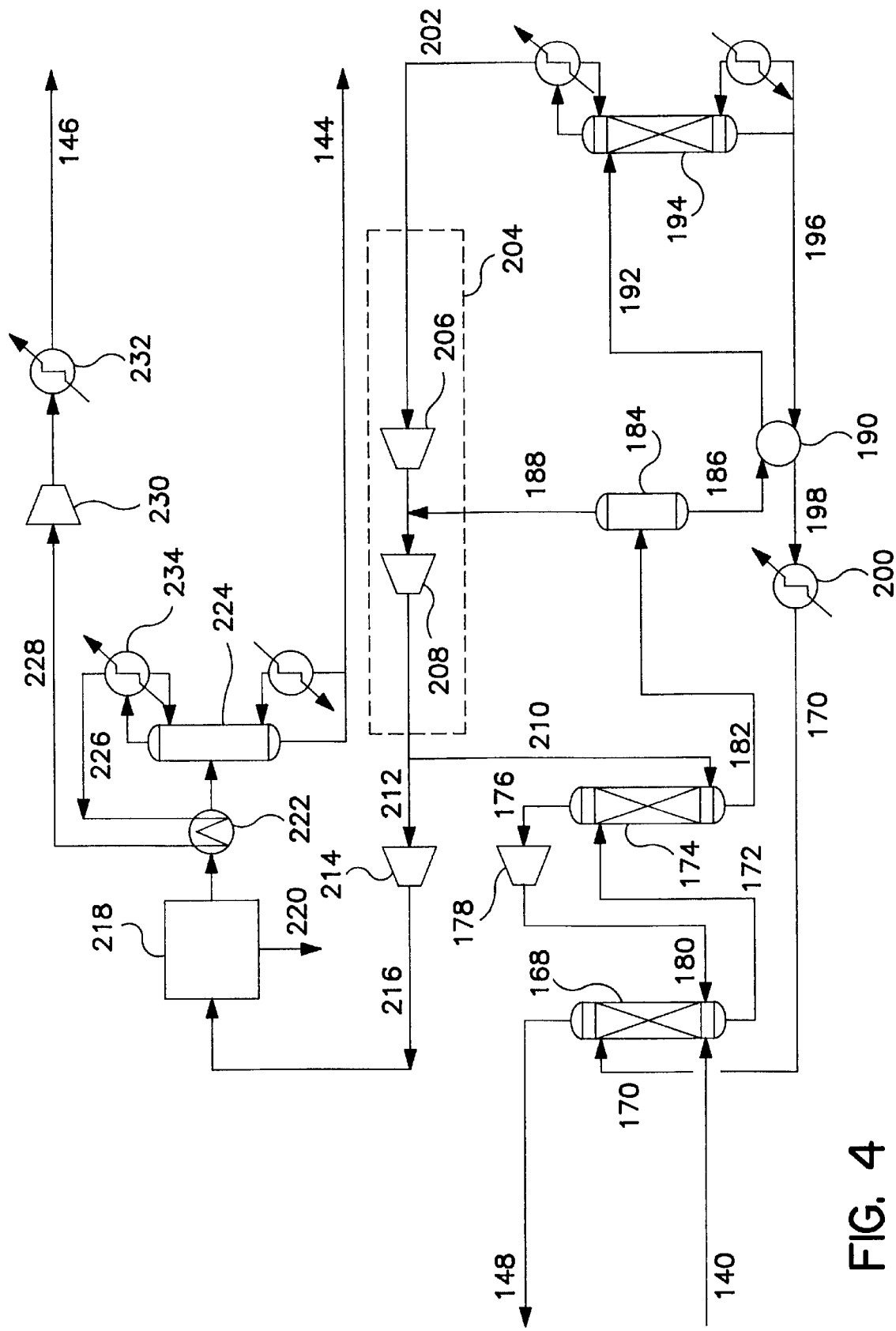
FIG. 4 is a process flow diagram illustrating the silver complexation absorption system used in the example in FIG. 3.

The process flowsheet of the silver complexation absorption system (142) that is used with the recycle mode of operation of FIG. 3 is given in FIG. 4. The unconverted methane (140) from the cycle gas compressor contains 61.1% methane, 10.2% ethylene, 0.9% propylene, 13.6% carbon dioxide, 2.7% oxygen, 2.9% ethane, 0.2% propane, 0.4% water, 1.5% carbon monoxide, 1.0% hydrogen, 5.4% nitrogen, and trace amounts of butene and butane, by weight. At 275 psia and 40° C., the unconverted methane enters the bottom of a conventional packed absorber (168) in which an aqueous solution of silver nitrate (170), at 35° C. and at an optimum concentration of 50% by weight, is employed to remove nearly all of the ethylene (99.9%) and propylene (98.9%). An increase in the strength of the silver nitrate solution reduces the solvent circulation rate but it also increases the silver inventory. Small quantities of nitric acid and hydrogen peroxide are added to the solution (not shown) to prevent silver reduction by hydrogen. In addition to the complexed ethylene and propylene, some of the light gas components such as hydrogen, methane, ethane, carbon monoxide, carbon dioxide, and oxygen physically dissolve into the rich solution (172) leaving the absorber. They are removed by reducing the pressure to 30 psia and using some of the olefin product gas (210) to strip them in the packed vent column (174). The overhead (176) from the vent column is recompressed to 275 psia by compressor 178 and returned (180) to the base of the absorber in order to recover the ethylene and propylene. The vent column tails stream (182) at 45° C., which is essentially free of light gases, is flashed down to atmospheric pressure in flash tank 184 to recover a portion of the ethylene (44%) and propylene (48%) that is contained in the rich solution. The rich solution (186) from the flash tank at 41° C. is preheated to 76° C. in heat exchanger 190 and sent (192) to the packed solvent recovery column (194) for final recovery of the remaining ethylene and propylene. The lean solution (196) from the tails of the solvent recovery column is cooled from 93° C. to 51° C. (198) by the cold feed (186) to the column in heat exchanger 190 and further cooled to 35° C. (170) with cooling water in cooler 200. The lean solution (170), which contains 5 ppm ethylene, is recycled to the top of absorber 168. The overhead olefin vapor (202) from the solvent recovery column at 9.3 psia is sent to the first stage (206) of the two-stage olefin gas compressor (204) and the vapor (188) from flash tank 184 is sent to the second stage (208). The final discharge pressure of 32 psia allows part of this stream (210) to be used as the stripping gas in vent column 174, while the remainder (212) becomes the crude olefins product that contains ethylene, propylene, water, and trace impurities. This stream is further compressed to 345 psia by compressor 214 and sent (216) to post treatment system 218 for removal (220) of trace levels of carbon monoxide (by copper oxide), oxygen (by metallic copper oxidation), carbon dioxide (by a caustic wash), and water (by molecular sieves). The treated olefins stream contains only ethylene and propylene, which are fractionated in a simple $C_2/C_3$ splitter column (224) operating at 310 psia to produce pipeline quality ethylene (226) as the overhead product and polymer grade propylene (144) as the tails product. The overhead ethylene (226) passes through heat exchanger 222 and the flow (228) is compressed to 825 psia by compressor 230 and cooled to 35° C. by cooler 232. The final product ethylene (146) is sent to an ethylene pipeline. The small condenser (234) on column 224 is the only operation in the entire process that requires refrigeration (−32° C. propylene).

EXAMPLE 2

Figure 5:
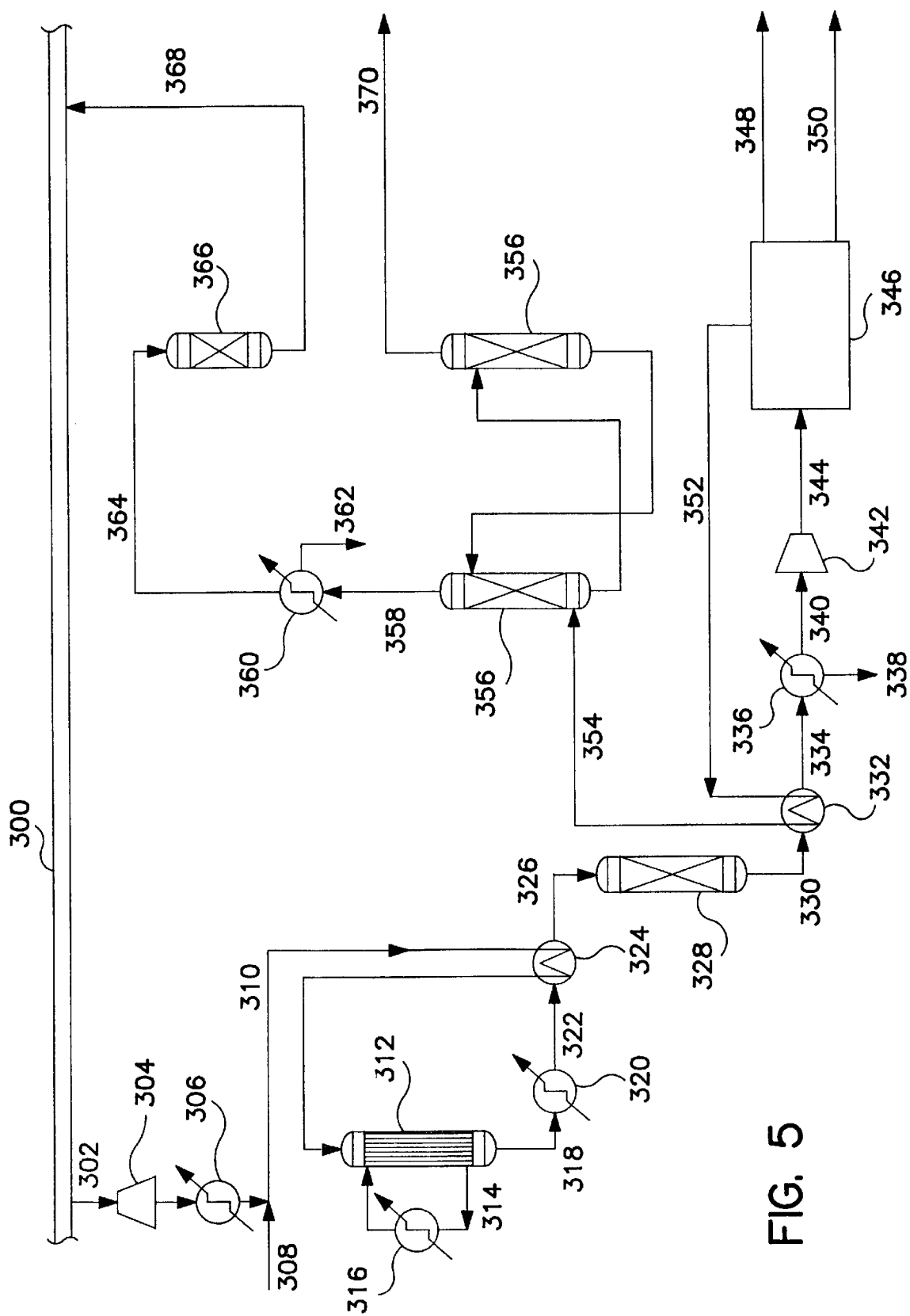
FIG. 5 is a process flow diagram illustrating an example of the single-pass mode of operation of the invention.

An example of the single-pass mode of operation is given by the process flow diagram in FIG. 5. In this example, the lower alkane is methane gas. Similar process flow diagrams can be derived for ethane or propane being the lower alkane by one skilled in the art by using the principles and guidelines illustrated. The methane gas (302) is processed natural gas from a natural gas pipeline (300) that has a pressure of 825 psia. The methane gas is expanded down to 275 psia by expander 304. The refrigeration from the resulting cold gas stream at −28° C. is recovered in heat exchanger 306 by chilling the circulating solvent in the silver complexation absorption system (346) that is given in FIG. 6. The warmed methane gas at 30° C. is then mixed with high purity oxygen (308) and the resulting cofeed feed gas mixture (310) is preheated to 250° C. by the hot reaction product (322) in heat exchanger 324 and fed to two fixed bed catalytic reactors (312) operating in parallel. The reactor feed contains 77.2% methane, 19.6% oxygen, 1.5% ethane, 1.2% carbon dioxide, 0.4% nitrogen, and a small amount of propane, by weight. The mole ratio of methane to oxygen is 7.8 and the oxygen concentration is 11% by volume. The oxidative dehydrogenation reaction temperature is maintained at about 540° C. by circulating molten salts (314) through the reactors. The salts are cooled in cooler 316 by generating 600 psig steam, which is consumed elsewhere in the process. The methane conversion is 20% and the product selectivity and distribution are the same as for the recycle mode case. The hot reactor product (318) at 215 psia is cooled to 300° C. by generating 600 psig steam in heat exchanger 320 and cooled to 120° C. by the cold reactor feed (310) in heat exchanger 324. The cooled reaction product gas (326) is fed to an adiabatic converter (328) in which 99.7% of the carbon monoxide byproduct is oxidized to carbon dioxide and 99.3% of the remaining oxygen is hydrogenated to water. This operation reduces the carbon monoxide and oxygen concentrations in the resulting off gas (330) to less than 10 ppm while simultaneously establishing a high oxygen conversion of 98.2%. The off gas (330) at 145° C. is cooled to 114° C. (334) in heat exchanger 332 by the cold vent stream (352) leaving the silver complexation absorption system (346) and is further cooled to 40° C. in cycle gas cooler 336, which removes most of the water (338). The cooled reaction product (340) is compressed by compressor 342 from 180 psia to 850 psia (344) and sent to the silver complexation absorption system (346), which will be described separately, in which ethylene (348) and propylene (350) are recovered selectively by complexation with a circulating silver nitrate solution. The unconverted methane gas (352) from this system at 30° C. is preheated to 93° C. (354) in heat exchanger 332 before entering a Benfield hot potassium carbonate unit (356) to remove 96% of the carbon dioxide (370), in order to increase the heating value of the unconverted methane gas up to about the level of pure methane or natural gas. The carbon dioxide absorber vent (358) at 107° C. is cooled to 40° C. in cooler 360, which removes water (362), and then the flow (364) is sent to molecular sieve drier 366, where the water concentration is reduced to 75 ppm prior to returning (368) the unconverted methane that contains ethane, propane, and other byproducts to the natural gas pipeline (300). The composition of the final return gas is about 94.6% methane, 2.4% ethane, 0.1% propane, 2.3% hydrogen, 0.4% nitrogen, and 0.2% carbon dioxide, with traces of 1-butene and butane, and 75 ppm water, 9 ppm oxygen, and 8 ppm carbon monoxide, by weight.

Figure 6:
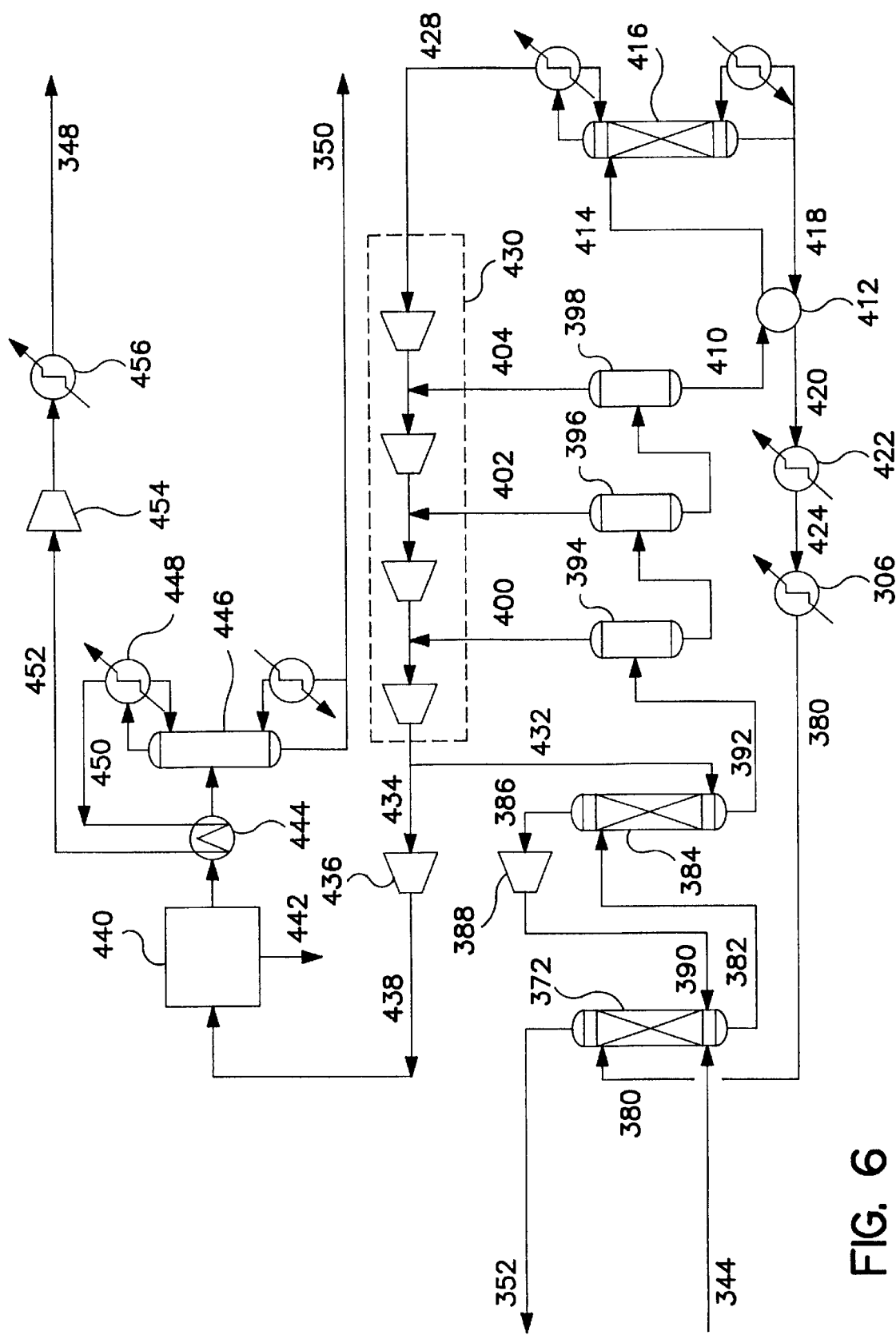
FIG. 6 is a process flow diagram illustrating the silver complexation absorption system used in the example in FIG. 5.

The process flowsheet of the silver complexation absorption system (346) that is used with the single-pass mode of operation of FIG. 5 is given in FIG. 6. The unconverted methane (344) from the cycle gas compressor contains 74.4% methane, 11.0% ethylene, 1.1% propylene, 8.7% carbon dioxide, 3.5% ethane, 0.2% propane, 0.2% water, 0.2% hydrogen, 0.5% nitrogen, and trace amounts of butene and butane, by weight. At 850 psia and 40° C., the unconverted methane enters the bottom of a conventional packed absorber (372) that uses an aqueous solution of silver nitrate (380) at 30° C. and 50% concentration by weight to remove nearly all of the ethylene (99.9%) and propylene (98.0%). The physically absorbed gases in the rich solution (382) leaving the absorber are removed by reducing the pressure to an optimum level of 150 psia and using some of the product gas (432) to strip the gases in packed vent column 384. The overhead (386) from the vent column is recompressed to 850 psia by compressor 388 and returned (390) to the base of the absorber. The vent column tails stream (392) at 50° C. is then flashed down to atmospheric pressure in three stages in flash tank 394 (65 psia), flash tank 396 (30 psia), and flash tank 398 (15 psia), in order to recover most of the ethylene (72%) and propylene (78%). The rich solution (410) from flash tank 398 at 36° C. is preheated to 68° C. in heat exchanger 412 and sent (414) to the solvent recovery column (416) for recovery of the remaining ethylene and propylene. The lean solution (418) from the tails of the solvent recovery column, which contains 5 ppm ethylene, is cooled from 86° C. to 46° C. (420) in heat exchanger 412 by the cold feed (410) to the column, cooled to 35° C. (424) in cooler 422 by cooling water, and chilled to 29° C. (380) in heat exchanger 306 by the expanded cold methane gas from FIG. 5. It is then recycled to the top of the absorber (372). The overhead olefin vapor (428) from the solvent recovery column at an optimum pressure of 7.3 psia is sent to the first stage of the four-stage olefin gas compressor (430), and the vapors (400, 402, 404) from each of the three flash tanks are routed to successively higher pressure stages in the cascade. The final discharge pressure of 155 psia allows a portion of this stream (432) to be used as the stripping gas for the vent column, while the remainder (434) becomes the crude olefins product that contains ethylene, propylene, water, and trace impurities. This stream is further compressed to 345 psia by compressor 436 and sent (438) to post treatment system 440, where trace quantities of carbon monoxide, carbon dioxide, oxygen, and water are removed (442). The treated olefins stream is fractionated in $C_2/C_3$ splitter column (446), which operates at 310 psia, to produce pipeline quality ethylene (450) and polymer grade propylene (350). The overhead ethylene (450) passes through heat exchanger 444 and the flow (452) is compressed to 825 psia by compressor 454 and cooled to 35° C. by cooler 456. The final product ethylene (348) is sent to an ethylene pipeline. The small condenser (448) on column 446 is the only operation that requires refrigeration.

EXAMPLE 3

Figure 7:
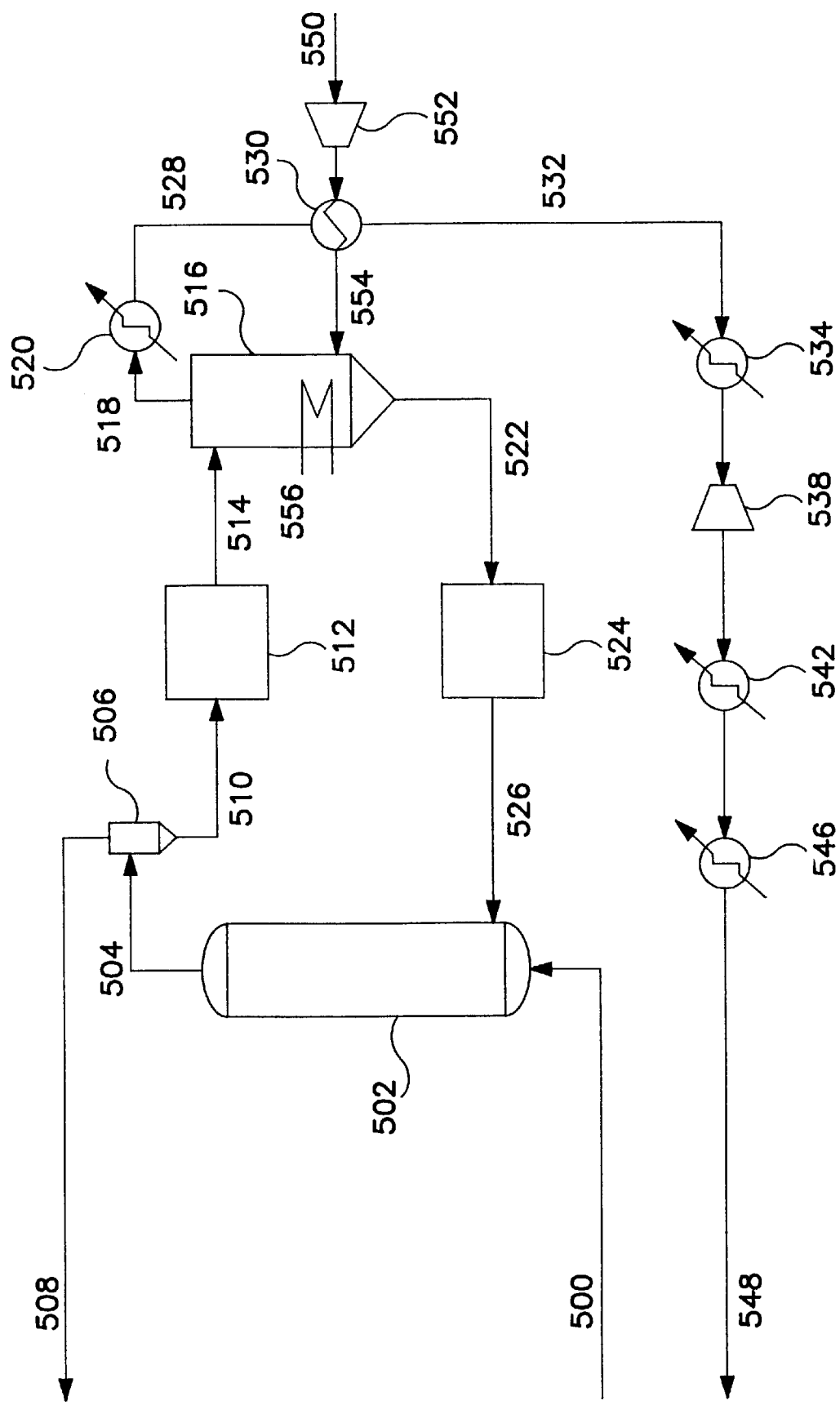
FIG. 7 is a process flow diagram illustrating an example of a circulating fluidized bed reaction system that may be used in the invention.

An example of a circulating fluidized bed reaction system that may be used as the oxidative dehydrogenation reaction process with either the recycle or single-pass modes of operation is illustrated by the process flowsheet given in FIG. 7. In this example, the lower alkane is methane gas. Similar process flow diagrams can be derived for ethane or propane being the lower alkane by one skilled in the art by using the principles and guidelines illustrated. The methane gas feed (500) to riser reactor 502 enters at 225 psia and 25° C. and is mixed in the reactor with fresh oxygen-containing catalyst (526) at 500° C. The spent catalyst and unconverted methane exit together (504) at the top of the reactor at 215 psia and 600° C. The unconverted methane (508) and spent catalyst (510) are separated in cyclone 506. Any residual methane, products, and byproducts that are adsorbed or entrained by the catalyst particles are optionally stripped from the catalyst in stripper 512. The spent catalyst (514) then enters the top of fluidized bed regenerator 516, where it is fluidized by hot air (554) injected at the bottom and oxidized by oxygen for reuse. The air feed (550) is compressed to about 215 psia by compressor 552 and preheated by heat exchanger 530. The catalyst is cooled in the regenerator from 600° C. to 500° C. by generating 600 psig steam (556). The regenerated catalyst (522) is optionally stripped of any residual free or unbound oxygen in stripper 524. The spent air (518) from the regenerator is cooled to 300° C.

(528) in heat exchanger 520 by generating 600 psig steam and is cooled to 180° C. in heat exchanger 530 by the cold air feed. The spent air (532) is then cooled to 40° C. in cooler 534 and is expanded from 205 psia to 25 psia and −76° C. in expander 538. The power recovered from this expansion is used by air compressor 552. The refrigeration is recovered in $C_2/C_3$ splitter condenser 542 and in solvent chiller 546 in the silver complexation absorption system. Because the circulating fluidized bed reaction system is simply an alternative to the fixed bed reactor illustrated for the recycle and single-pass modes, the remaining aspects of the overall process are the same as shown in FIGS. 3 and 5.

Alternatively, high purity oxygen may be used instead of air in the circulating fluidized bed reaction system of FIG. 7. If oxygen is substituted for air, compressor 552, its associated steam turbine and condenser, and lean air expander 538 are not required. But eliminating expander 538 also eliminates the cold air that is used for refrigeration. The reduced flow of gas also significantly reduces the size of regenerator 516. Because excess oxygen leaving the top of the regenerator can be recycled to the base by a small compressor, the energy recovery system can be eliminated. Therefore all of the 600 psig steam generation occurs in the regenerator, and exchanger 530 and cooler 534 can be eliminated.

What is claimed is:

1. A method for producing olefins from at least one lower alkane by oxidative dehydrogenation, which comprises:
   (1) supplying at least one lower alkane;
   (2) providing a source of oxygen;
   (3) converting a portion of the lower alkane by an oxidative dehydrogenation reaction process that utilizes a catalyst, to produce unconverted lower alkane containing at least one olefin product, at least one alkane byproduct, and water, wherein the reaction pressure is at least about 50 psi and the olefin product and the alkane byproduct are formed from the lower alkane with a combined selectivity of at least about 40%;
   (4) removing water from the unconverted lower alkane;
   (5) recovering the at least one olefin product from the unconverted lower alkane by using a complexation separation that utilizes at least one complexation agent to selectively remove olefins from non-olefins and which is not a membrane separation; and
   (6) recycling after steps (4) and (5) a majority of the unconverted lower alkane which contains the at least one alkane byproduct to the oxidative dehydrogenation reaction process of step (3).

2. The method of claim 1, wherein the lower alkane is one of methane and ethane.

3. The method of claim 1, wherein the complexation separation utilizes a π-bond complex to selectively remove olefins from non-olefins.

4. The method of claim 1, wherein the reaction temperature is less than about 700° C.

5. The method of claim 1, wherein the reaction pressure is in the range of from about 100 psi to about 400 psi.

6. The method of claim 1, wherein the mole ratio of olefin product to alkane byproduct in step (3) is at least about 1/1.

7. The method of claim 2, wherein the at least one olefin product is ethylene and the at least one alkane byproduct is ethane.

8. The method of claim 1, wherein the oxidative dehydrogenation reaction process utilizes a fixed bed reactor or a fluidized bed reactor with cofeed of lower alkane and oxygen.

9. The method of claim 1, wherein the oxidative dehydrogenation reaction process utilizes a circulating fluidized bed reaction system in which a lower alkane feed is contacted with oxidized catalyst in a riser reactor to form a reduced catalyst and the reduced catalyst from the riser reactor is re-oxidized by using air or oxygen in a fluidized bed regenerator.

10. The method of claim 1, wherein at least a majority of the recycled at least one alkane byproduct is oxidatively dehydrogenated to form at least one olefin product.

11. The method of claim 1 further comprising removing carbon dioxide from the unconverted lower alkane prior to step (6).

12. The method of claim 1 further comprising adding a purge of the unconverted lower alkane which contains the at least one alkane byproduct to a methane gas transport system.

13. The method of claim 1, wherein the complexation separation is an absorption separation and the complexation agent selectively absorbs ethylene and propylene, without substantially absorbing higher olefins.

14. The method of claim 1, wherein the complexation separation is an absorption separation and the complexation agent contains a silver (I) ion.

15. The method of claim 14, wherein the complexation agent is aqueous silver nitrate.

16. The method of claim 1, wherein the catalyst exhibits higher selectivity for olefin product and alkane byproduct at the reaction pressure used for oxidative dehydrogenation than the catalyst or catalyst precursor exhibits at a pressure in the range of about atmospheric pressure to about 25 psig.

17. The method of claim 1, wherein the catalyst is capable of oxidatively dehydrogenating the at least one alkane byproduct to form at least one olefin.

18. The method of claim 1, wherein the catalyst is one of a promoted transition metal oxide catalyst and a promoted rare earth oxide catalyst.

19. The method of claim 18, wherein the catalyst is selected from the group consisting of $Mn/Na_2WO_4$, $Sr/La_2O_3$, and $Sr/Sm_2O_3$.

20. The method of claim 1, wherein the catalyst is selected from the group consisting of a rare earth oxycarbonate catalyst, a rare earth hydroxycarbonate catalyst, and a rare earth carbonate catalyst.

21. The method of claim 20, wherein the catalyst comprises a nonstoichiometric rare earth oxycarbonate of the formula $M_XC_YO_Z$ having a disordered and/or defect structure, wherein M is at least one rare earth element selected from the group consisting of La, Pr, Nd, Sm, Eu, Gd, Tb, Dy, Ho, Er, and Tm; X=2; Z=3+AY; A is less than about 1.8; and Y is the number of carbon atoms in the oxycarbonate, and said catalyst, when used for the oxidative dehydrogenation of said lower alkane at a pressure above about 100 psig, has a selectivity of at least about 40% to olefin product and alkane byproduct.

22. The method of claim 1 further comprising subsequently converting the at least one olefin product recovered in step (5) into at least one olefin derivative, wherein the production rate of said at least one olefin is substantially the same as the supply rate of said at least one olefin required to manufacture said at least one olefin derivative at a desired production rate, and said at least one olefin derivatives is selected from the group consisting of polyolefins, ethylene-propylene rubber, ethylene oxide, ethylene glycol, ethanol, and hydrocarbon fuel.

23. A method for producing ethylene and/or propylene from at least one lower alkane by oxidative dehydrogenation, which comprises:

(1) supplying at least one lower alkane;

(2) providing a source of oxygen;

(3) converting a portion of the lower alkane by an oxidative dehydrogenation reaction process that utilizes a rare earth oxycarbonate catalyst, to produce unconverted lower alkane containing at least ethylene and/or propylene, at least one alkane byproduct and/or at least one higher olefin, and water, wherein the reaction pressure is at least about 75 psi and olefin and alkane byproduct are formed from the lower alkane with a combined selectivity of at least about 40% and a mole ratio of olefin to alkane byproduct of at least about 1/1;

(4) removing water from the unconverted lower alkane;

(5) recovering ethylene and/or propylene from the unconverted lower alkane by using an aqueous complexation absorption separation that utilizes at least one complexation agent containing a silver (I) ion to selectively remove ethylene and/or propylene from higher olefins and non-olefins and which is not a membrane separation; and (6) recycling after steps (4) and (5) a majority of the unconverted lower alkane which contains the at least one alkane byproduct and/or higher olefin to the oxidative dehydrogenation reaction process of step (3).

24. The method of claim 23, wherein the lower alkane is methane.

25. A method for producing olefins from at least one lower alkane by oxidative dehydrogenation, wherein recycling of unconverted lower alkane containing reaction byproducts is reduced or eliminated, which comprises:

(1) supplying at least one lower alkane;

(2) providing a source of oxygen;

(3) converting a portion of the lower alkane by an oxidative dehydrogenation reaction process that utilizes a catalyst, wherein the reaction pressure is at least about 50 psi, to produce unconverted lower alkane containing at least one olefin product, at least one combustible byproduct, and water;

(4) removing water from the unconverted methane;

(5) recovering the at least one olefin product from the unconverted lower alkane by using a complexation separation that utilizes at least one complexation agent to selectively remove olefins from non-olefins and which is not a membrane separation; and (6) adding after steps (4) and (5) a majority of the unconverted lower alkane which contains the at least one combustible byproduct to a methane gas transport system.

26. The method of claim 25, wherein the at least one lower alkane in step (1) is processed natural gas supplied from a natural gas transport system, and the methane gas transport system of step (6) is the natural gas transport system of step (1).

27. The process of claim 26, wherein said natural gas transport system is a natural gas pipeline.

28. The method of claim 25 further comprising removing carbon dioxide from the unconverted lower alkane prior to step (6).

29. The method of claim 1 in which the unconverted lower alkane which contains the at least one alkane by product of step (6) being a gaseous effluent having substantially the same heating value as natural gas is added to a natural gas transport system.

30. The method of claim 1, wherein the complexation separation is an absorption sepration and the complexation agent contains a copper (I) ion.

31. The method of claim 1, wherein the complexation separation is an absorption separation that utilizes a mixture of complexation agents comprising silver and copper salts.

* * * * *